United States Patent
Sullivan

(10) Patent No.: US 7,339,042 B2
(45) Date of Patent: Mar. 4, 2008

(54) GENE DELIVERY TO TUMORS

(75) Inventor: Sean M. Sullivan, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 405 days.

(21) Appl. No.: 10/864,774

(22) Filed: Jun. 9, 2004

(65) Prior Publication Data

US 2005/0090646 A1  Apr. 28, 2005

Related U.S. Application Data

(60) Provisional application No. 60/557,030, filed on Mar. 26, 2004, provisional application No. 60/476,941, filed on Jun. 9, 2003.

(51) Int. Cl.
  *C07H 21/02* (2006.01)
  *C07H 21/04* (2006.01)
(52) U.S. Cl. ..................... 536/23.1; 536/23.4
(58) Field of Classification Search ................ 536/23.1
  See application file for complete search history.

(56) References Cited

U.S. PATENT DOCUMENTS

2003/0104622 A1  6/2003  Robbins et al.

OTHER PUBLICATIONS

Gura (Science, 1997, 278:1041-1042.).*
Mai et al (Nov. 1, 2001, Cancer Research, 61:7709-7712).*
Freshney (Culture of Animal Cells, A Manual of Basic Technique, Alan R. Liss, Inc., 1983, New York, p. 4).*
Dermer (Bio/Technology, 1994, 12:320).*
Mai et al., A Proapoptotic Peptide for the Treatment of Solid Tumors, Cancer Res., 61:7709-7712, Nov. 1, 2001.

* cited by examiner

*Primary Examiner*—Misook Yu
*Assistant Examiner*—Sean E Aeder
(74) *Attorney, Agent, or Firm*—Akerman Senterfitt

(57) ABSTRACT

Disclosed are methods and compositions for gene therapy for tumors. Cytotoxic agents are selectively expressed in endothelial cells of tumor blood vessels, and delivered to tumor cells adjacent to the blood vessels, producing a bystander effect such that all the cells in contact with the transfected cells are killed or permanently growth arrested. In particular, cytotoxic gene products secreted from the transfected cell using a secretory signal sequence, include a membrane permeability domain at the N- or C-terminus that can shuttle the cytotoxic domain into non-transfected cells and back into transfected cells.

4 Claims, 16 Drawing Sheets

Cross Sectional View of Transfected Tumor Blood Vessel

Transfected Endothelial Cell

Untransfected Tumor Cell

Day 6	Day 11	Day 14

SEQUENCE LISTING

```
<160> NUMBER OF SEQ ID NOS: 18

<210> SEQ ID NO 1
<211> LENGTH: 15
<212> TYPE: PRT
<213> ORGANISM: Unknown
<220> FEATURE:
<223> OTHER INFORMATION: TAT-Based MPD Fusion Peptide

<400> SEQUENCE: 1

Ala Gly Gly Gly Tyr Gly Arg Lys Lys Arg Arg Gln Arg Arg Arg
1               5                   10                  15

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 14
<212> TYPE: PRT
<213> ORGANISM: Homo sapiens

<400> SEQUENCE: 3

Met Val Arg Arg Phe Leu Val Thr Leu Arg Ile Arg Arg Ala
1               5                   10

<210> SEQ ID NO 4
<211> LENGTH: 14
```

-continued

```
<212> TYPE: PRT
<213> ORGANISM: Rattus norvegicus

<400> SEQUENCE: 4

Met Gly Arg Arg Phe Val Val Thr Val Arg Ile Arg Arg Thr
1               5                   10

<210> SEQ ID NO 5
<211> LENGTH: 14
<212> TYPE: PRT
<213> ORGANISM: Mus musculus

<400> SEQUENCE: 5

Met Gly Arg Arg Phe Leu Val Thr Val Arg Ile Gln Arg Ala
1               5                   10

<210> SEQ ID NO 6
<211> LENGTH: 18
<212> TYPE: PRT
<213> ORGANISM: Homo sapiens

<400> SEQUENCE: 6

Gly Cys Gly Thr Cys Gly Gly Gly Cys Cys Thr Ala Ala Ala Thr
1               5                   10                  15

Cys Cys

<210> SEQ ID NO 7
<211> LENGTH: 18
<212> TYPE: PRT
<213> ORGANISM: Homo sapiens

<400> SEQUENCE: 7

Cys Cys Cys Ala Gly Cys Thr Cys Gly Ala Gly Ala Cys Cys Ala Cys
1               5                   10                  15

Gly Cys

<210> SEQ ID NO 8
<211> LENGTH: 50
<212> TYPE: PRT
<213> ORGANISM: Rattus norvegicus

<400> SEQUENCE: 8

Gly Ala Thr Cys Thr Gly Thr Ala Cys Thr Thr Cys Ala Thr Ala Cys
1               5                   10                  15

Thr Thr Thr Thr Cys Ala Thr Thr Cys Cys Ala Ala Thr Gly Gly Gly
                20                  25                  30

Gly Thr Gly Ala Cys Thr Thr Thr Gly Cys Thr Thr Cys Thr Gly Gly
                35                  40                  45

Ala Gly
        50

<210> SEQ ID NO 9
<211> LENGTH: 50
<212> TYPE: PRT
<213> ORGANISM: Rattus norvegicus

<400> SEQUENCE: 9

Ala Cys Ala Thr Gly Ala Ala Gly Thr Ala Thr Gly Ala Ala Ala Ala
1               5                   10                  15

Gly Thr Ala Ala Gly Gly Thr Thr Ala Cys Cys Cys Ala Cys Thr
                20                  25                  30
```

```
Gly Ala Ala Ala Cys Gly Ala Ala Gly Ala Cys Cys Thr Cys Cys Thr
        35                  40                  45
Ala Gly
    50

<210> SEQ ID NO 10
<211> LENGTH: 21
<212> TYPE: PRT
<213> ORGANISM: Rattus norvegicus

<400> SEQUENCE: 10

Gly Cys Cys Gly Thr Ala Ala Thr Ala Thr Cys Ala Gly Cys Thr
1               5                   10                  15
Gly Ala Ala Cys Gly
            20

<210> SEQ ID NO 11
<211> LENGTH: 26
<212> TYPE: PRT
<213> ORGANISM: Rattus norvegicus

<400> SEQUENCE: 11

Gly Cys Ala Ala Gly Thr Cys Gly Ala Cys Cys Thr Ala Thr Ala Ala
1               5                   10                  15
Thr Gly Cys Cys Gly Thr Ala Met Arg Ala
            20                  25

<210> SEQ ID NO 12
<211> LENGTH: 21
<212> TYPE: PRT
<213> ORGANISM: Rattus norvegicus

<400> SEQUENCE: 12

Cys Cys Ala Gly Cys Cys Thr Cys Gly Gly Ala Cys Thr Cys Thr
1               5                   10                  15
Ala Gly Ala Gly Gly
            20

<210> SEQ ID NO 13
<211> LENGTH: 10
<212> TYPE: PRT
<213> ORGANISM: Human immunodeficiency virus

<400> SEQUENCE: 13

Tyr Gly Arg Lys Lys Arg Arg Gln Arg Arg
1               5                   10

<210> SEQ ID NO 14
<211> LENGTH: 16
<212> TYPE: PRT
<213> ORGANISM: Unknown
<220> FEATURE:
<223> OTHER INFORMATION: Drosophila

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 14
<212> TYPE: PRT
<213> ORGANISM: Homo sapiens

<400> SEQUENCE: 15
```

```
Met Val Arg Arg Phe Leu Val Thr Leu Arg Ile Arg Arg Ala
1               5                   10

<210> SEQ ID NO 16
<211> LENGTH: 29
<212> TYPE: PRT
<213> ORGANISM: Unknown
<220> FEATURE:
<223> OTHER INFORMATION: TAT-P14 ARF

<400> SEQUENCE: 16

Ala Gly Gly Gly Tyr Gly Arg Lys Lys Arg Arg Gln Arg Arg Met
1               5                   10                  15

Val Arg Arg Phe Leu Val Thr Leu Arg Ile Arg Arg Ala
            20                  25

<210> SEQ ID NO 17
<211> LENGTH: 29
<212> TYPE: PRT
<213> ORGANISM: Unknown
<220> FEATURE:
<223> OTHER INFORMATION: P14 ARF-TAT

<400> SEQUENCE: 17

Met Val Arg Arg Phe Leu Val Thr Leu Arg Ile Arg Arg Ala Ala Gly
1               5                   10                  15

Gly Gly Tyr Gly Arg Lys Lys Arg Arg Gln Arg Arg Arg
            20                  25

<210> SEQ ID NO 18
<211> LENGTH: 30
<212> TYPE: PRT
<213> ORGANISM: Unknown
<220> FEATURE:
<223> OTHER INFORMATION: ANT-P14RF

<400> SEQUENCE: 18

Arg Gln Ile Lys Ile Trp Phe Gln Asn Arg Arg Met Lys Trp Lys Lys
1               5                   10                  15

Met Val Arg Arg Phe Leu Val Thr Leu Arg Ile Arg Arg Ala
            20                  25                  30
```

GENE DELIVERY TO TUMORS

This application claims the benefit of provisional U.S. application U.S. Ser. No. 60/476,941 filed Jun. 9, 2003 and provisional U.S. application U.S. Ser. No. 60/557,030 filed Mar. 26, 2004 which are hereby incorporated by reference in their entirety.

FIELD OF THE INVENTION

The invention relates to gene therapy methods of targeting cytotoxic agents to tumor cells and endothelial cells in the blood vessels of tumors. In particular, the invention relates to a gene transfer system to tumor endothelium for the purpose of expression proteins that will inhibit tumor progression of the brain tumor to minimize distribution through the body by being secreted into the circulation.

BACKGROUND

There are an estimated 359,000 people living with a diagnosis of a brain tumor in the U.S. Of these tumors, 17,000 are new malignant primary brain tumors and 170,000 are metastatic tumors derived mainly from breast and lung cancer as of 2002. There were an estimated 13,100 deaths per year due to glioma based brain tumors with glioblastoma multiformae being the most aggressive and lethal.

Therapy for treatment of brain cancer is difficult for the following reasons: 1.) Patients are usually diagnosed 6 months to a year before death. Hence, a significant tumor mass is already established by the time treatment is initiated (2) The cancer cells invade normal tissue and do not establish defined barriers, thus surgery yields incomplete removal of residual tumor cells. (3) The brain is protected from the external environment by the blood brain barrier. This barrier is compromised in regions of the brain but there are areas that are still protected and thus accessibility to chemotherapy is restricted. The potency of standard chemotherapy is further reduced by expression of P-glycoprotein encoded by the multidrug resistance-1 (MDR) gene in capillary endothelium of brain capillaries. (4) Many primary tumors metastasize to the brain yielding multiple lesions further complicating therapy. (5) The knowledge base for brain cancer is greatly reduced in comparison to other types of cancer. Making it difficult to define molecular targets and also predicting the course of the disease. Standard therapy is surgical resection and postoperative radiation. Due to the tumor location, complete removal of the tumor may not be possible and some gliomas are completely inoperable.

Gene therapy, the delivery of a therapeutic nucleic acid to a diseased tissue, offers an alternative approach to traditional cancer treatments. In a typical application, genes are targeted to tumor cells to kill the cell or halt the cell's progression through the mitotic cycle. A significant problem in gene therapy-mediated cancer treatment is targeting the gene therapy agent preferentially to cancer cells rather than non-cancerous cells.

Thus there is an urgent need in the art to target therapeutic molecules to cancer cells without affecting the surrounding normal tissue.

SUMMARY

The invention relates to the development of cytotoxic fusion proteins that are useful for selectively killing endothelial cells in blood vessels that feed tumors. The fusion proteins include a membrane permeability domain (MPD) fused to a cytotoxic domain. The MPD allows the fusion protein to cross a cell membrane, while the cytotoxic domain kills the cell. Some versions of the cytotoxic fusion proteins are engineered to be secreted from endothelial cells and to enter adjacent tumor cells, thereby killing these cells by a "bystander" mechanism.

In a preferred embodiment, the invention provides a cytotoxic fusion protein comprising an MPD and a cell toxicity domain. The MPD of the fusion protein can be a Tat peptide, derived from the HIV virus. The MPD can have the amino acid sequence as set forth in SEQ ID NO's 1-2, SEQ ID NO: 8, SEQ ID NO: 9, and SEQ ID NO: 10.

In a preferred embodiment, the invention provides a cytotoxic fusion protein comprising a membrane permeability domain, signal sequence and a cell cytotoxic domain. Preferably, the cell cytotoxic domain is lethal for tumor cells.

In another preferred embodiment, the membrane permeability domain comprises an HIV Tat peptide, PTD-5 and/or *Drosophila* antenapedia homeodomain.

In another preferred embodiment, the cytotoxic fusion protein comprising a membrane permeability domain penetrates tumor cells, non-tumor cells, endothelial cells. Preferably, the cytotoxic domain is cytolytic for tumor cells and non-cytolytic for non-tumor cells.

In another preferred embodiment, the membrane permeability domain comprises any one of the sequences as set forth in SEQ ID NO's 1-2, SEQ ID NO: 8, SEQ ID NO: 9, and SEQ ID NO: 10, variants or fragments thereof.

In another preferred embodiment, the invention provides for membrane permeability domains which are about 45% homologous to any one of SEQ ID NO's 1-2, SEQ ID NO: 8, SEQ ID NO: 9, and SEQ ID NO: 10; preferably, the membrane permeability domains are about 55% homologous to any one of SEQ ID NO's 1-2, SEQ ID NO: 8, SEQ ID NO: 9, and SEQ ID NO: 10; preferably, the membrane permeability domains are about 65% homologous to any one of SEQ ID NO's 1-2, SEQ ID NO: 8, SEQ ID NO: 9, and SEQ ID NO: 10; preferably, the membrane permeability domains are about 75% homologous to any one of SEQ ID NO's 1-2, SEQ ID NO: 8, SEQ ID NO: 9, and SEQ ID NO: 10; preferably, the membrane permeability domains are about 85% homologous to any one of SEQ ID NO's 1-2, SEQ ID NO: 8, SEQ ID NO: 9, and SEQ ID NO: 10; preferably, the membrane permeability domains are 90%, 91%, 92%, 93%, 94%, 95%, 96%, 97%, 98%; 99% and 99.9% homologous to any one of SEQ ID NO's 1-2, SEQ ID NO: 8, SEQ ID NO: 9, and SEQ ID NO: 10.

In another preferred embodiment, the cytolytic domain of the cytotoxic fusion protein comprises a p16 peptide, p19 peptide and/or p14ARF peptide, fragments or variants thereof.

In another preferred embodiment, the cytolytic domain is about 45% homologous to p16; preferably, the cytolytic domain is about 55% homologous to p16; preferably, the cytolytic domain is about 65% homologous to p16; preferably, the cytolytic domain is about 75% homologous to p16; preferably, the cytolytic domain is about 85% homologous to p16; preferably, the cytolytic domain is 90%, 91%, 92%, 93%, 94%, 95%, 96%, 97%, 98%; 99and 99.9% homologous p16.

In another preferred embodiment, the cytolytic domain is about 45% homologous to p14ARF; preferably, the cytolytic domain is about 55% homologous to p14ARF; preferably, the cytolytic domain is about 65% homologous to p14ARF; preferably, the cytolytic domain is about 75% homologous to p14ARF; preferably, the cytolytic domain is about 85% homologous to p14ARF; preferably, the cytolytic domain is 90%, 91%, 92%, 93%, 94%, 95%, 96%, 97%, 98%; 99% and 99.9% homologous to p14ARF.

In another preferred embodiment, the cell cytolytic domain of the fusion protein comprises the amino acid sequence as set forth in SEQ ID NO's: 3-5 and or p14ARF, variants or fragments thereof.

In another preferred embodiment, the fusion protein comprises the membrane permeability domain identified by any one of SEQ ID NO's 1-2, SEQ ID NO: 8, SEQ ID NO: 9, and SEQ ID NO: 10, a signal sequence and a cell cytolytic domain identified by SEQ ID NO: 3-5 and/or p14ARF variants, fragments or combinations thereof.

In another preferred embodiment, the invention provides an expression vector comprising a nucleic acid encoding the fusion protein comprising a membrane permeability domain, a signal sequence and a cytolytic domain as described supra.

In another preferred embodiment, the expression vector preferably comprises a promoter that selectively drives expression in endothelial cells and/or proliferating cells. For example, the vector can include a promoter that selectively drives expression of the fusion protein in endothelial cells, or a promoter that selectively drives such expression in proliferating cells. Preferably the promoter is 4×ETe/cdc6, variants or fragments thereof as described in detail in the Examples which follow.

In another preferred embodiment, the invention provides an endothelial cell comprising vector encoding a membrane permeability domain, signal sequence and a cytolytic domain. Preferably, the cytolytic domain is cytolytic for tumor cells and non-lethal for normal cells. The membrane permeability domain can be 5' to the cytolytic domain or 3' to the cytolytic domain.

In another preferred embodiment, the endothelial cell comprising the vector further comprises a nucleic acid encoding a cytotoxic fusion protein that is secreted from the cell. Preferably, the endothelial cell comprising the vector, is located within a blood vessel of a tumor, and the expressed fusion protein is secreted from the endothelial cell and enters a tumor cell.

In another preferred embodiment, the invention provides a method of killing a cell comprising the step of contacting the cell with the cytotoxic fusion protein as described supra, and explained in detail in the Examples which follow.

In another preferred embodiment, the cell is a tumor cell and can be proliferating or non-proliferating.

In another preferred embodiment, the invention provides a method of killing a cell comprising the steps of:
(a) providing a cell and;
(b) administering to the cell a vector comprising a nucleic acid encoding a fusion protein as described supra, and detailed in the Examples which follow.

In another preferred embodiment, the invention provides a method of treating a subject suffering from or susceptible to a tumor, comprising the steps of:
(a) providing a subject having a tumor comprising at least one tumor cell; and
(b) contacting the tumor cell with the cytotoxic fusion protein.

In accordance with the invention the endothelial cells in blood vessels of the tumor are transduced with the vector expressing a cytotoxic fusion protein wherein the cytotoxic fusion protein is vectorially secreted from the endothelial cell and enters the tumor cell. The endothelial cell can be within a blood vessel of a tumor, and the fusion protein can be engineered to be secreted from the endothelial cell, entering the cells of the tumor by means of its MPD.

Preferably, the cell cytotoxic domain of the fusion protein is a p16 peptide, and/or P14ARF variants or fragments thereof. P16 is an inhibitory regulator of the cell cycle. In some embodiments, the cell toxicity domain can have the amino acid sequence as set forth in SEQ ID NO: 2. In preferred embodiments of the proliferating endothelial cell vector, the promoter can be 4×ETe/cdc6.

In another preferred embodiment, the invention provides a method for treating a tumor in an animal subject, the method comprising the step of administering to the animal subject a composition comprising a chimeric fusion molecule composition, as described above. Preferably, the chimeric fusion molecule composition is administered with one or more therapeutic agents and/or adjuvants.

In other preferred embodiments, the therapeutic agents comprise antiangiogenic antibodies, tumor antigen specific antibodies, glycolysis inhibitor agents, anti-angiogenic agents, chemotherapeutic agents, radiotherapy, radionuclides, or drugs that ameliorate the symptoms of a patient.

In accordance with the invention, the chimeric fusion molecule composition is administered to a patient in combination with metronomic therapy. For example, administration of continuous low-doses of the chimeric fusion molecule and one or more therapeutic agents. Therapeutic agents can include, for example, chemotherapeutic agents such as, cyclophosphamide (CTX, 25 mg/kg/day, p.o.), taxanes (paclitaxel or docetaxel), busulfan, cisplatin, cyclophosphamide, methotrexate, daunorubicin, doxorubicin, melphalan, cladribine, vincristine, vinblastine, and chlorambucil.

Other aspects of the invention are described infra.

DETAILED DESCRIPTION

Figure 1:
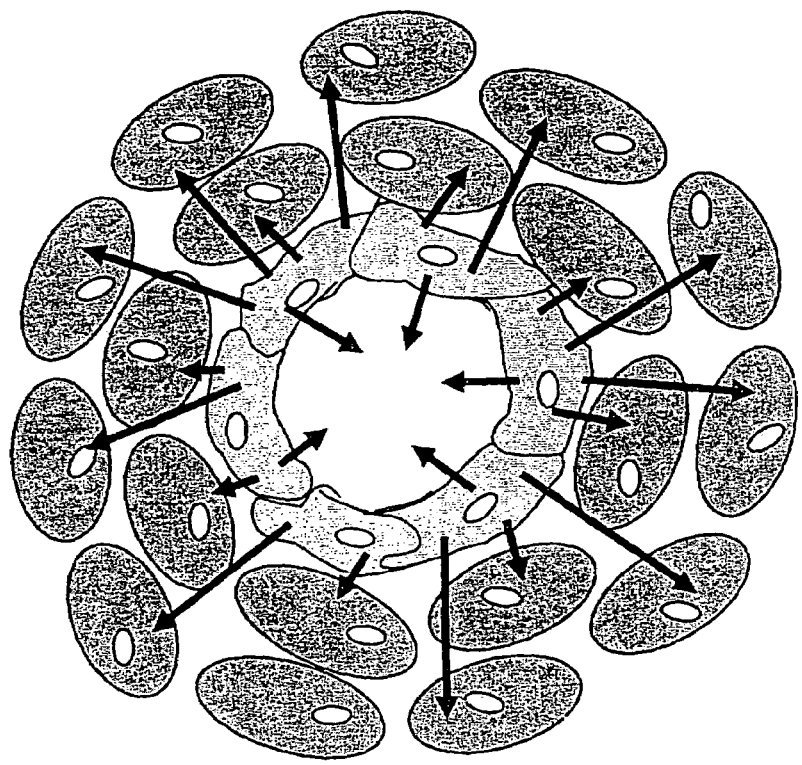
FIG. 1 is a schematic diagram showing targeted gene delivery to tumor blood vessel endothelium and adjacent tumor cells. Outward-pointing arrows indicate delivery of cytotoxic fusion proteins from transfected endothelial cells to tumor cells.
Figure 1:
Figure 1:
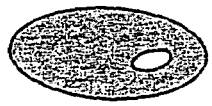

The invention provides compositions and methods for limiting growth of tumors. Selective killing or arrest of cell division in tumor cells is achieved by means of fusion proteins composed of a membrane permeability domain (MPD) and a cytotoxic domain. The MPD enables the effector protein to enter a tumor cell by crossing the cell membrane. Upon entry into the cell, the cytotoxic domain of the protein functions to prevent cell division by interfering with regulatory proteins of the cell cycle.

Definitions

Prior to setting forth the invention, definitions of certain terms which are used in this disclosure are set forth below:

As used herein, the singular forms "a", "an" and "the" include plural referents unless the context clearly dictates otherwise.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

The term "subject," as used herein, means a human or non-human animal, including but not limited to mammals such as a dog, cat, horse, cow, pig, sheep, goat, chicken, primate, rat, and mouse.

An "expression vector" is a vector capable of expressing a DNA (or cDNA) molecule cloned into the vector and, in certain cases, producing a polypeptide or protein. Appropriate transcriptional and/or translational control sequences are included in the vector to allow it to be expressed in a cell. Expression of the cloned sequences occurs when the expression vector is introduced into an appropriate host cell. If a eukaryotic expression vector is employed, then the appropriate host cell would be any eukaryotic cell capable of expressing the cloned sequences.

As used herein, the term "administering a molecule to a cell" (e.g., an expression vector, nucleic acid, a angiogenic factor, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the trans forming DNA. A "clone" is a population of cells derived from a single cell or common ancestor by mitosis. A "cell line" is a clone of a primary cell that is capable of stable growth in vitro for many generations (e.g., at least about 10).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a)

an alternative linking group, (b) an analogous form of purine, (c) an analogous form of pyrimidine, or (d) an analogous sugar, all as described herein.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "oligonucleotide" refers to a polynucleotide formed from naturally occurring bases and pentofuranosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art are able to select other linkages for use in practice of the invention.

Oligonucleotides may also include species which include at least some modified base forms. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_nNH_2$ or $O(CH_2)_nCH_3$ where n is from 1 to about 10, and other substituents having similar properties.

The terms "homologous", "homology", "sequence homology" can be used interchangeably and indicate a relative degree of sequence identity between two or more biologically relevant sequences. Homology can be determined, for example, between two peptide sequences by aligning the sequences to obtain a best alignment or a preferred alignment (programs such as FASTA in the case of peptide sequences can be helpful); the number of identical amino acids in the alignment and the total number of amino acids are counted; and the homology is usually represented as a percentage (the ratio of identical units to total units, amino acids in this example, multiplied by one hundred).

As used herein "chimeric fusion molecule" comprises membrane permeability sequences, if desired a signal sequence and a cytolytic molecule genetically fused together. The membrane permeability sequence and/or the signal sequence can be located 5' or 3' to the cytolytic molecule.

The term "membrane permeability domain" or "MPD" is used to indicate a peptide, or derivative thereof, that directs the transport of a peptide, protein, or molecule associated with the MPD; from the outside of a cell into the cytoplasm of the cell through a cytoplasmic membrane of the cell. Furthermore, a peptide that contains a "membrane permeability domain" and additional amino acid sequences could be used as a "membrane transport sequence" for the purposes of the present invention. An MPD may be composed of D- or L-amino acids.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, "cancer" refers to all types of cancer or neoplasm or malignant tumors found in mammals, including, but not limited to: leukernias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma.

Additional cancers which can be treated the chimeric fusion molecule according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

The "treatment of cancer or tumor cells", refers to an amount of chimeric fusion molecule, described throughout the specification and in the Examples which follow, capable of invoking one or more of the following effects: (1) inhibition, to some extent, of tumor growth, including, (i) slowing down (ii) inhibiting angiogenesis and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, "metronomic" therapy refers to the administration of continuous low-doses of a therapeutic agent and/or chimeric fusion molecule described herein.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety.

In a preferred embodiment, the invention provides expression vectors for targeted delivery and expression of the cytotoxic fusion proteins in proliferating (dividing) endothelial cells. Proliferating endothelial cells are highly enriched in the new blood vessels that are essential for maintenance and growth of tumors. Accordingly, by targeting delivery to these cells, normal vasculature is spared, and abnormal endothelium and the adjacent tumor cells are prevented from dividing upon expression of the cytotoxic fusion protein. Therefore, transfection of the endothelial cells results in an anti-angiogenic effect.

In another preferred embodiment, the invention provides a chimeric fusion protein that is designed to facilitate "bystander" delivery of the cytotoxic fusion proteins to the tumor cells adjacent to the transfected blood vessel. FIG. 1 is a schematic illustration of the disclosed therapeutic approach to simultaneously targeting endothelial cells and tumor cells. Various aspects of the design are further described in detail below.

Preferably, the therapeutic proteins can be engineered to be secreted from the tumor endothelium and diffuse into adjacent tumor cells and untransfected tumor endothelial cells resulting in the killing of these cells.

In a preferred embodiment, signal sequences are placed upstream of the cytotoxic therapeutic gene resulting in the secretion of the protein from the cell. Membrane permeability sequences, derived from HIV Tat and the homeodomain of antennapedia (ANT) are preferably placed upstream of the cytotoxic domain to facilitate cell entry of the cytotoxic domain into untransfected cells.

In accordance with the invention, fusion molecules of the invention comprising, for example, Tat and ANT peptides, can enter glioblastomas, gliomas and endothelial cells.

In another preferred embodiment, the invention provides for targeted delivery of cell killing protein (cytolytic) to eliminate any unwanted side effects due to expression in non-cancerous tissue. In accordance with the invention, several safe guards restricting expression to tumor endothelium are implemented. Non-limiting examples include: 1.) administration of the complexes intra-arterially for first pass access to the tumor; (2.) ligand directed gene delivery to proliferating endothelial cells; (3) selective expression by a promoter only active in proliferating endothelium and (4) preferential basolateral secretion from the endothelium into the interstitium.

Membrane Permeable Cytotoxic Fusion Proteins

In a preferred embodiment, the invention provides a fusion protein that incorporates a membrane permeability domain (MPD) and a cell cytotoxic domain. Preferably, the cell cytotoxic domain is cytotoxic for tumor cells. For example, if an anti-cancer therapeutic protein or peptide comprising a cytotoxic domain enters a cancer cell, the cell can be killed or arrested from dividing. To achieve transport of the fusion proteins into cancer cells, the fusion proteins are designed to include a MPD. The presence of a MPD in a protein or peptide enables it to cross the plasma membrane of a cell. Thus, if a MPD-bearing protein comes into contact with a cancerous cell, the chimeric fusion protein crosses the plasma membrane and enters the cell. FIG. 1 shows a diagrammatic illustration of a small blood vessel (composed of endothelial cells) in a tumor, surrounded by tumor cells, which are dependent upon the blood supply for their survival. The arrows in FIG. 1 schematically indicate the movement of MPD-comprising fusion proteins of the invention across the cell membranes of the tumor cells, following secretion of these proteins from transfected endothelial cells.

In a preferred embodiment, any MPD can be used that enables a protein or peptide to cross the membrane of a cell. Proteins and peptide sequences known to be effective as MPDs have been identified in the Tat protein of HIV (Nagahara H et al., *Nature Med* 4:1449-1452, 1998; Gius D R et al., *Cancer Res.* 59:2577-2580, 1999) and in the antennapedia (ANT) homeodomain in *Drosophila*. In certain preferred embodiments of the invention, effective transport of the fusion protein into cancer cells in vitro and endothelial cells of tumor blood vessels in vivo was achieved using a Tat-based MPD having 11 amino acids from the Tat sequence and a 4-amino acid bridge sequence (AGGG) used for attaching tags such as fluorophores. The amino acid sequence of this MPD has the following sequence:

AGGGYGRKKRRQRRR. (SEQ ID NO:1)

In a preferred embodiment, the invention provides membrane permeability domains which are about 45% homologous to SEQ ID NO: 1; preferably, the membrane permeability domains are about 55% homologous to SEQ ID NO: 1; preferably, the membrane permeability domains are about 65% homologous to SEQ ID NO: 1; preferably, the membrane permeability domains are about 75% homologous to SEQ ID NO: 1; preferably, the membrane permeability domains are about 85% homologous to SEQ ID NO: 1; preferably, the membrane permeability domains are 90%, 91%, 92%, 93%, 94%, 95%, 96%, 97%, 98%; 99% and 99.9% homologous to SEQ ID NO: 1.

In another preferred embodiment, the MPD is an antennaepedia homeodomain. Preferably, the MPD is identified by the sequence: RQIKIWFQNRRMKWKK (SEQ ID NO 2).

In another preferred embodiment, the membrane permeability domains are identified by anyone of SEQ ID NO 1, SEQ ID NO 2, SEQ ID NO: 7, SEQ ID NO: 8, and SEQ ID NO: 9;

In a preferred embodiment, the invention provides membrane permeability domains which are about 45% homologous to SEQ ID NO: 2; preferably, the membrane permeability domains are about 55% homologous to SEQ ID NO: 2; preferably, the membrane permeability domains are about 65% homologous to SEQ ID NO: 2; preferably, the membrane permeability domains are about 75% homologous to SEQ ID NO: 2; preferably, the membrane permeability domains are about 85% homologous to SEQ ID NO: 2; preferably, the membrane permeability domains are 90%, 91%, 92%, 93%, 94%, 95%, 96%, 97%, 98%; 99% and 99.9% homologous to SEQ ID NO: 2.

In another preferred embodiment, the invention provides for membrane permeability domains which are about 45% homologous to any one of SEQ ID NO's 1-2, SEQ ID NO: 8, SEQ ID NO: 9, and SEQ ID NO: 10; preferably, the membrane permeability domains are about 55% homologous to any one of SEQ ID NO's 1-2, SEQ ID NO: 8, SEQ ID NO: 9, and SEQ ID NO: 10; preferably, the membrane permeability domains are about 65% homologous to any one of SEQ ID NO's 1-2, SEQ ID NO: 8, SEQ ID NO: 9, and SEQ ID NO: 10; preferably, the membrane permeability domains are about 75% homologous to any one of SEQ ID NO's 1-2, SEQ ID NO: 8, SEQ ID NO: 9, and SEQ ID NO: 10; preferably, the membrane permeability domains are about 85% homologous to any one of SEQ ID NO's 1-2, SEQ ID NO: 8, SEQ ID NO: 9, and SEQ ID NO: 10; preferably, the membrane permeability domains are 90%, 91%, 92%, 93%, 94%, 95%, 96%, 97%, 98%; 99% and 99.9% homologous to any one of SEQ ID NO's 1-2, SEQ ID NO: 8, SEQ ID NO: 9, and SEQ ID NO: 10.

All MPD domains encompassed by this invention have the function of mediating translocation across a cell membrane from outside the cell to the interior of the cell. Such MPD domains could potentially be modified such that they lose the ability to export a protein but maintain the ability to import molecules into the cell. Preferably, a signal sequence is also included to provide specificity for any selected cell type.

Signal peptides can be selected, for example, from the SIGPEP database, which also lists the origin of the signal peptide. When a specific cell type is to be targeted, a signal peptide used by that cell type can be chosen. For example, signal peptides encoded by a particular oncogene can be selected for use in targeting cells in which the oncogene is expressed. Additionally, signal peptides endogenous to the cell type can be chosen for importing biologically active molecules into that cell type. And again, any selected signal peptide can be routinely tested for the ability to translocate across the cell membrane of any given cell type according to the teachings herein. Specifically, the signal peptide of choice can be conjugated to a biologically active molecule, e.g., a functional domain of a cellular protein such as P16, P14ARF or a reporter construct, and administered to a cell, and the cell is subsequently screened for the presence of the active molecule. The presence of modified amino acids in the signal peptide can additionally be useful for rendering a complex, wherein the biologically active molecule is a peptide, polypeptide or protein, more resistant to peptidase in the subject. Thus these signal peptides can allow for more effective treatment by allowing more peptides to reach their target and by prolonging the life of the peptide before it is degraded. Additionally, one can modify the amino acid sequence of the signal peptide to alter any proteolytic cleavage site present in the original signal sequence for removing the signal sequence. Clearage sites are characterized by small, positively charged amino acids with no side chains and are localized within about 1 to about 4 amino acids from the carboxy end of the signal peptide.

Another example of a useful signal peptide is the signal peptide from Capasso fibroblast growth factor (K-FGF). Any signal peptide, however, capable of translocating across the cell membrane into the interior of the selected target cell can be used according to this invention.

By "linked" as used herein is meant that the biologically active molecule is associated with the MPD in such a manner that when the MPD crosses the cell membrane, the molecule is also imported across the cell membrane. Examples of such means of linking include (1) when the molecule is a peptide, the MPD (and a nuclear localization peptide, if desired) can be linked by a peptide bond, i.e., the two peptides can be synthesized contiguously; (2) when the molecule is a polypeptide or a protein (including antibody), the signal peptide (and a nuclear localization peptide, if desired). can be linked to the molecule by a peptide bond or by a non-peptide covalent bond (such as conjugating a signal peptide to a protein with a cross-linking reagent); (3) for molecules that have a negative charge, such as nucleic acids, the molecule and the signal peptide (and a nuclear localization peptide, if desired) can be joined by charge-association between the negatively charged molecule and the positively-charged amino acids in the peptide or by other types of association between nucleic acids and amino acids; (4) chemical ligation methods can be employed to create a covalent bond between the carboxy-terminal amino acid of the signal peptide (and a nuclear localization peptide, if desired) and the molecule.

Cytotoxic Domain of Fusion Proteins

The biologically active cytotoxicity domain of the fusion protein is the portion of the fusion protein that mediates cell killing. Any type of cytotoxic domain capable of being incorporated into a fusion protein can be used in the invention. An advantageous cytotoxic domain for control of cancer cells is one that inhibits the cell cycle. The cell cycle is the process whereby a cell replicates its DNA, forms a duplicate set of chromosomes, and subsequently divides into two daughter cells. It is divided into phases known as $G_1$, S (for DNA Synthesis), $G_2$, and M (for Mitosis). Transit through the cell cycle is necessary for the growth and proliferation of tumor cells. Fusion proteins of the invention utilize negative regulators of the cell cycle, in order to prevent cells from dividing and thereby arrest growth of abnormal cells.

Control of the cell cycle is a complex process involving a large number of regulatory factors, including many known cell cycle inhibitors (CCIs). Uncontrolled proliferation in tumors containing chromosomal deletions and mutations in CCIs (for example, gliomas and astrocytomas) can be reversed by expression of normal copies of CCIs in these cells. Under prolonged conditions, in some cases apoptosis is induced (Gius D R et al., Cancer Res. 59:2577-2580).

Any CCI domain effective for the purpose can be used in the fusion proteins of the invention. Two families of CCIs, i.e., INK4 and CIP/KIP are presently known. Genes from each of these families encode CCIs that prevent the progression from $G_1$ through to the S phase of the cell cycle (Ragione F D et al., J Biol Chem 271:15942-9, 1996; Katayose Y et al., Cancer Res 57: 5441-5, 1997).

Figure 2:
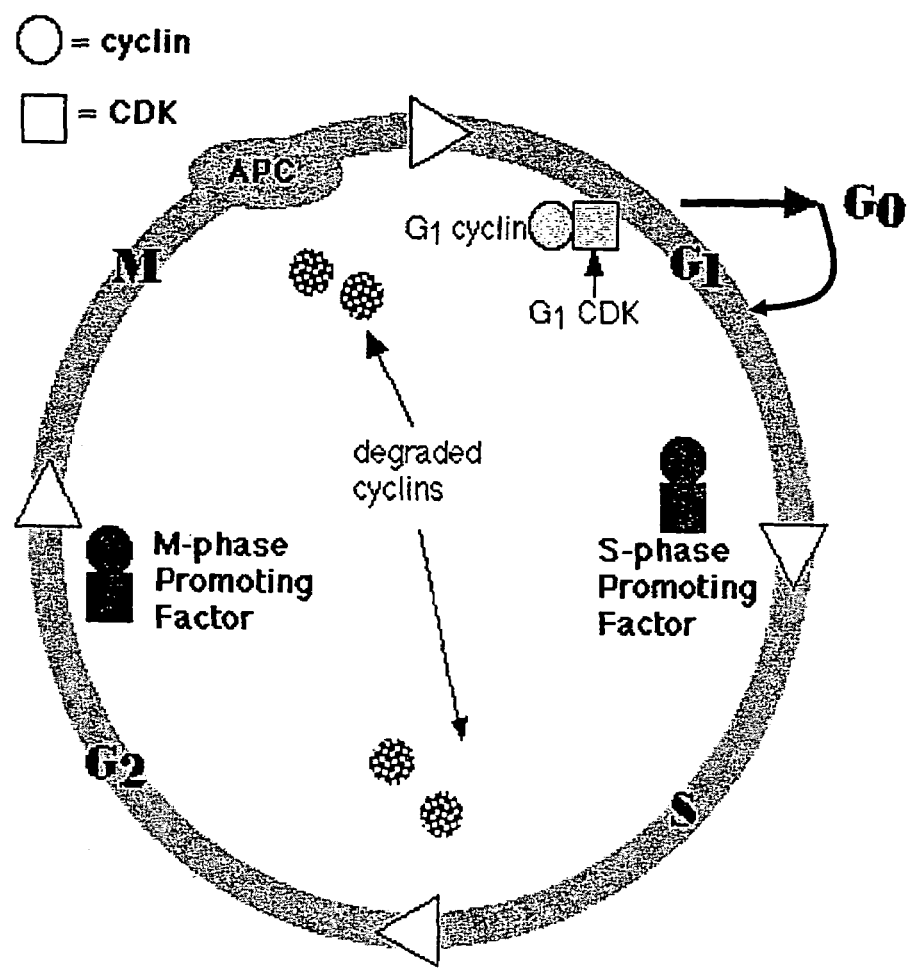
FIG. 2 is a schematic diagram showing regulation of the cell cycle by cyclins and cyclin-dependent kinases (CDKs).

As shown in FIG. 2, regulation of the cell cycle is mediated in part by two major families of proteins, i.e., the cyclins, and the cyclin-dependent kinases (CDKs). The cyclins are divided into classes (G1, S-phase and M-phase cyclins) according to their time of maximal activity during the cell cycle. The levels of each class of cyclin rise and fall at different stages of the cell cycle. Progression through the cell cycle is mediated by the cyclin-dependent kinases (CDKs). Like the cyclins, the CDKs are divided into three classes ($G_1$, S-phase, and M-phase). In order to be activated, the CDKs must bind to the appropriate cyclin (FIG. 2). Once activated, the CDKs phosphorylate protein substrates that control processes in the cell cycle.

Figure 3:
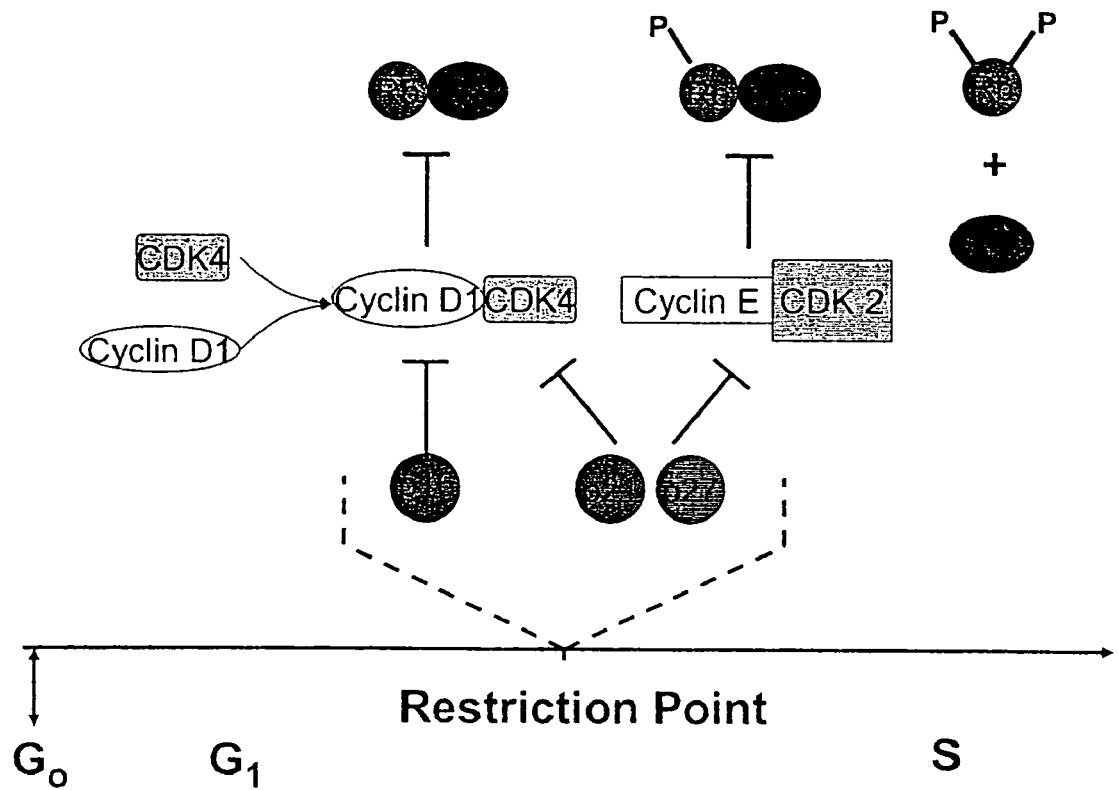
FIG. 3 is a diagram showing regulation of the $G_1$ phase of the cell cycle by interaction of cyclins with various CDKs, i.e., p16, p21, and p27.

Use of activated CDK complexes as CCIs is effective for control of the cell cycle because as described above, $G_1$ CDKs are essential for progression from $G_1$ into S-phase. Preferred embodiments of the fusion proteins of the invention utilize a peptide sequence from the p16 protein as a CCI. Referring to FIG. 3, p16 binds to CDK 4 (and CDK 6), inhibiting association of these proteins with cyclin D, and therefore preventing the cell from entering the S-phase. The p27 protein is an inhibitor of the CDK2-cyclin E and CDK2-cyclin A complexes. Sequences from the p16 and p27 genes have been used as CCIs, and when overexpressed in transfected cells can cause complete arrest of cells in G1 (Patel et al., Mol Ther 2:161-169, 2000; Lamphere L et al., J Mol Med 78:451-259, 2000; Nagahara H et al., Nature Med 4:1449-52; Gius D R et al., Cancer Res 59:2577-80, 1999).

Cyclin dependent kinase inhibitors (CDKi's) are proteins which regulate the activity of cyclin-dependent kinase (CDK)/cyclin complexes which play a key role in the cell cycle. CDK/cyclin complexes are comprised of a catalytic kinase subunit (such as cdc2, CDK2, CDK4, or CDK6) with one of a variety of regulatory cyclin subunits (such as cyclin A, B 1, B2, D1, D2, D3, or E) which results in the assembly of functionally distinct CDK/cyclin complexes.

Thus, in accordance with the invention, by "cyclin dependent kinase inhibitor (CDKi)" is meant any protein which inhibits and/or regulates a CDK/cyclin complex. The definition includes, without limitation, proteins from the CIP/KIP family of CDKi proteins which includes, without limitation, human p14ARF, rat p19 ARF, human $p27_{kip1}$ (GenBank Accession No. U10906, Polyak et al. (1994) Cell 78:56-66); murine $p27_{kip1}$ (GenBank Accession No. U09968, Polyak et al. (1994) Cell 78:56-66); $p27_{kip1}$ (GenBank Accession Nos. D86924 and D83792, Nomura et al. (1997) Gene 191(2):211-218); human $p57_{KIP\,2}$ (GenBank Accession No. NM000076, Matsuoka et al. (1995) Genes Dev. 9(6):650-662); murine $p57_{KIP2}$ (GenBank Accession No. U20553, Lee et al. (1995) Genes Dev. 9(6):639-649); canine $p21_{Waf1/Cip1}$ (GenBank Accession No. AF076469); and human $p21_{Waf1/Cip1}$ (GenBank Accession No. L25610; Harper et al. (1993) Cell 75:806-816, 1993); as well as proteins from the INK4 family of CDKi proteins which includes, without limitation, human $p18_{CDKN2C}$ (GenBank Accession Nos. AF041248 and NM001262, Blais et al. (1998) Biochem. Biophys. Res. Commun. 247(1):146-153); human Cdi1 (GenBank Accession No. NM005192, Gyuris et al. (1993) Cell 75(4):791-803); human $p19_{INK4d}$ (GenBank Accession No. NM001800, Guan et al. (1996) Mol. Biol. Cell 7(1):57-70); human p15 (GenBank Accession No. S75756, Jen et al. (1994) Cancer Res. 54(24):6353-6358); murine $p19^{INK4d}$ (GenBank Accession Nos. U80415, U79634, and U79639); murine $p16_{Ink4d/MTS1}$ (GenBank Accession Nos. AF044336 and AF044335, Zhang et al. (1998) Proc. Natl. Acad. Sci. USA 95(5):2429-2434); and human $p16_{INK4}$ (GenBank Accession No. NM.sub.— 000077; Serrano et al. (1993) Nature 366(6456):704-707 and Okamoto et al. (1994) Proc. Natl. Acad. Sci. USA 91(23): 11045-11049). Exemplary CDKi's according to the invention are the fusion proteins described herein and described in PCT Publication No. WO99/06540, hereby incorporated by reference.

In preferred embodiments of the invention, the CCI domain of the fusion protein is a peptide encoded by exon 1 of p16. This exon is common to three CCIs of this family, i.e. p14, p16 and p19. The peptide sequences of exon 1 of p16 in the human, rat, and mouse, respectively, are the following:

MVRRFLVTLRIRRA (SEQ ID NO: 3) Human p16 exon 1
MGRRFVVTVRIRRT (SEQ ID NO: 4) Rat p16 exon 1
MGRRFLVTVRIQRA (SEQ ID NO: 5) Mouse p16 exon 1

In another preferred, the cyclin dependent kinase inhibitor is a protein from the CIP/KIP family or an active fragment thereof. For example, the cyclin dependent kinase inhibitor is a protein from the INK4 family or an active fragment thereof, such as human p16 protein or an active fragment thereof. By "active fragment" is meant a polypeptide that encompasses at least the amino acid sequence required for inhibition of the appropriate cyclin dependent kinase which is targeted by the indicated CDKi (e.g., for human p27, see, Russo et. al. (1998) *Nature* 395:237-243). In a preferred embodiment, the cyclin dependent kinase inhibitor is derived from a mammal (e.g., a human).

Other examples of biologically active molecules include proteins, polypeptides and peptides, which include functional domains of biologically active molecules, such as growth factors, enzymes, transcription factors, toxins, antigenic peptides (as for vaccines), antibodies, and antibody fragments. Additional examples of biologically active molecules include nucleic acids, such as plasmids, coding DNA sequences, mRNAs and antisense RNA molecules, carbohydrates, lipids and glycolipids.

Fusion Proteins with Tat and p16 Sequences

In several preferred embodiments of the invention, the fusion proteins are hybrids comprising sequences from Tat and the first exon of p16. Studies using synthetic peptides containing these sequences demonstrated that the arrangement of the two domains of the fusion protein (i.e., Tat-p16 or P16-Tat) was not critical to the effectiveness of the proteins for cell killing. Studies with fluorescently labeled embodiments of these peptides injected into the lumena of isolated blood vessels demonstrated that they are taken up by the endothelial cells of intact blood vessels.

Chimeric molecules can be prepared using conventional techniques in molecular biology or protein chemistry. Where the chimeric molecule is a fusion protein, molecular biology methods can be used to join two or more genes in frame into a single nucleic acid. The nucleic acid can then be expressed in an appropriate host cell under conditions in which the chimeric molecule is produced. A carrier domain might also be conjugated (e.g., covalently bonded) to a cytotoxic domain by other methods known in the art for conjugating two such molecules together. For example, the p14ARF can be chemically derivatized with a carrier domain either directly or using a linker (spacer). Several methods and reagents (e.g., cross-linkers) for mediating this conjugation are known. See, e.g., catalog of Pierce Chemical Company; and Means and Feeney, *Chemical Modification of Proteins*, Holden-Day Inc., San Francisco, Calif. 1971; "Monoclonal Antibody—Toxin Conjugates: Aiming the Magic Bullet," Thorpe et al., *Monoclonal Antibodies in Clinical Medicine*, Academic Press, pp. 168-190 (1982); Waldmann (1991) *Science*, 252: 1657; and U.S. Pat. Nos. 4,545,985 and 4,894,443.

A cytolytic domain may be fused of conjugated to a carrier domain in various orientations. For example, the carrier domain may be joined to either the amino or carboxy termini of a cytolytic domain. The cytolytic domain may also be joined to an internal region of the carrier domain, or conversely, the carrier domain may be joined to an internal location of the anti-angiogenic agent domain.

In some circumstances, it is desirable to free the carrier domain from the cytolytic domain when the chimeric molecule has reached its target site. Therefore, chimeric conjugates featuring linkages that are cleavable in the vicinity of the target site may be used when one of the domains is to be released at the target site. Cleaving of the linkage to release the carrier domain from the cytolytic domain may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used. A number of different cleavable linkers are known to those of skill in the art. See, e.g., U.S. Pat. Nos. 4,618,492; 4,542,225; and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to proteins one skilled in the art are able to determine a suitable method for attaching a given carrier domain to a cytolytic domain.

In another preferred embodiment, carrier domains within the invention facilitate purification of the chimeric molecule. Any molecule known to facilitate-purification of a chimeric molecule can be used. Representative examples of such carrier domains include antibody fragments and affinity tags (e.g., GST, HIS, FLAG, and HA). Chimeric molecules containing an affinity tag can be purified using immunoaffinity techniques (e.g., agarose affinity gels, glutathione-agarose beads, antibodies, and nickel column chromatography). Chimeric molecules that contain an Ig domain as a carrier domain can be purified using immunoaffinity chromatography techniques known in the art (e.g., protein A or protein G chromatography).

Other carrier domains within the invention that can be used to purify the chimeric molecule can be readily identified by testing the molecules in a functional assay. For instance, a molecule can be screened for suitability as a carrier domain by fusing the molecule to an cytolytic agent and testing the fusion for purity and yield in an in vitro assay. The purity of recombinant proteins can be estimated by conventional techniques, for example, SDS-PAGE followed by the staining of gels with Coomassie-Blue.

In one embodiment, the chimeric molecule construct is a fusion (poly)peptide or a mosaic (poly)peptide. The fusion (poly)peptide may comprise merely the domains of the constructs as described herein, as well as (a) functional fragment(s) thereof. However, it is also envisaged that the fusion (poly)peptide comprises further domains and/or functional stretches. Therefore, the fusion (poly)peptide can comprise at least one further domain, this domain being linked by covalent or non-covalent bonds. The linkage as well as the construction of such constructs, can be based on genetic fusion according to the methods described herein or known in the art (e.g., Sambrook et al., loc. cit., Ausubel, "Current Protocols in Molecular Biology", Green Publishing Associates and Wiley Interscience, N.Y. (1989)) or can be performed by, e.g., chemical cross-linking as described in, e.g., WO 94/04686. The additional domain present in the construct may be linked by a flexible linker, such as a (poly)peptide linker, wherein the (poly)peptide linker can comprises plural, hydrophilic, peptide-bonded amino acids of a length sufficient to span the distance between the C-terminal end of the further domain and the N-terminal end of the peptide, (poly)peptide or antibody or vice versa. The linker may, inter alia, be a Glycine, a Serine and/or a Glycine/Serine linker. Additional linkers comprise oligomerization domains. Oligomerization domains can facilitate the combination of two or several antigens or fragments thereof in one functional molecule. Non-limiting examples of oligomerization domains comprise leucine zippers (like jun-fos, GCN4, E/EBP; Kostelny, *J. Immunol.* 148 (1992), 1547-1553; Zeng, *Proc. Natl. Acad. Sci.* USA 94 (1997), 3673-3678, Williams, *Genes Dev.* 5 (1991), 1553-1563; Suter, "Phage Display of Peptides and Proteins", Chapter 11, (1996), Academic Press), antibody-derived oligomerization domains, like constant domains $C_H1$ and $C_L$ (Mueller, *FEBS Letters* 422 (1998), 259-264) and/or tetramerization domains like $GCN_4$-LI (Zerangue, *Proc. Natl. Acad. Sci.* USA 97 (2000), 3591-3595).

Furthermore, the chimeric fusion construct to be used in the present invention, as described herein, may comprise at least one further domain, inter alia, domains which provide for purification means, like, e.g. histidine stretches. The further domain(s) may be linked by covalent or non-covalent bonds.

The linkage can be based on genetic fusion according to the methods known in the art and described herein or can be performed by, e.g., chemical cross-linking as described in, e.g., WO 94/04686. The additional domain present in the construct may be linked by a flexible linker, such as a polypeptide linker to one of the binding site domains; the polypeptide linker can comprise plural, hydrophilic or peptide-bonded amino acids of a length sufficient to span the distance between the C-terminal end of one of the domains and the N-terminal end of the other of the domains when the polypeptide assumes a conformation suitable for binding when disposed in aqueous solution.

As an illustrative example which is not meant to limit or construe the invention in any way, the following is provided. Synthetic peptides derived from HIV Tat (TAT) and the antenapedia homeodomain from *drosophila* (ANT) were tested for their cell penetration properties in brain tumor cell lines and rat brain arteries. Both fluorescein labeled Tat and ANT peptides displayed periplasmic punctate staining around the cell nucleus for both human glioblastoma cell lines and a rat glioma cell line. A 14 amino acid sequence derived from P14ARF was added to the C-terminus of Tat and ANT peptides. The Tat-P14ARF peptide produced nuclear staining whereas the ANT-P14ARF peptide showed only intracellular punctate staining. Cell viability studies showed that both TatP14ARF and ANTP14ARF were toxic to brain tumor cells. Cell killing by Tat-P14ARF peptide was more potent than ANT-P14ARF peptide yielding an $_{IC50}$ of 3 µM. Exchanging the P14ARF domain and the Tat domain for the N-terminus and C-Terminus, respectively, decreased the $_{IC50}$ from 9 µM to 3 µM. Intraluminal administration of the fluorescent peptides into pressure mounted cerebral arteries showed only endothelial cell staining and not smooth muscle cell staining. The Tat peptide stained the nucleus whereas the ANT peptide yielded diffuse cytoplasmic staining. Extraluminal addition labeled only smooth muscle cells and not the endothelial cells. Addition of the cell-killing domain did not inhibit peptide uptake by either cell type and did not change the staining pattern. The impact of Tat-P14ARF on the biological activity of the pressure-mounted arteries was tested by measuring the response to vasodilation and vasoconstriction conditions. Intraluminal addition of Tat-P14ARF inhibited endothelial cell response to histamine and bradykinin, whereas the smooth muscle response to hypertonic and hypotonic solutions of KCL was unaffected.

This example, which is described in further detail in the Examples which follow, characterize the ability of cell penetration peptides to enter brain tumor cells and non-tumor cells, such as endothelial cells and smooth muscle cells.

Modified Chimeric Molecules

The constructs of the present invention may comprise domains originating from one species, e.g., from mammals, such as human. However, chimeric and/or humanized constructs are also envisaged and within the scope of the present invention.

Furthermore, the polynucleotide/nucleic acid molecules of the invention may comprise, for example, thioester bonds and/or nucleotide analogues. The modifications may be useful for the stabilization of the nucleic acid molecule, e.g., against endo- and/or exonucleases in the cell. These nucleic acid molecules may be transcribed by an appropriate vector containing a chimeric gene which allows for the transcription of the nucleic acid molecule in the cell. The polynucleotide/nucleic acid molecules of the invention may be a recombinantly produced chimeric nucleic acid molecule comprising any of the aforementioned nucleic acid molecules either alone or in combination. The polynucleotide may be, e.g., DNA, cDNA, RNA or synthetically produced DNA or RNA or a recombinantly produced chimeric nucleic acid molecule comprising any of those polynucleotides either alone or in combination. The polynucleotide can be part of a vector, e.g., an expression vector, including, e.g., recombinant viruses. The vectors may comprise further genes, such as marker genes, that allow for the selection of the vector in a suitable host cell and under suitable conditions.

In one aspect, the polynucleotides of the invention are operatively linked to expression control sequences allowing expression in prokaryotic or eukaryotic cells. Expression of the polynucleotide comprises transcription of the polynucleotide into a translatable mRNA. Regulatory elements ensuring expression in cells, including eukaryotic cells, such as mammalian cells, are well known to those skilled in the art. They usually comprise regulatory sequences ensuring initiation of transcription, and, optionally, poly-A signals ensuring termination of transcription and stabilization of the transcript. Additional regulatory elements may include transcriptional as well as translational enhancers, and/or naturally-associated or heterologous promoter regions. Exemplary regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. The nucleic acids of the invention can also comprise, in addition to elements responsible for the initiation of transcription, other elements, such regulatory elements and transcription termination signals, such as the SV40-poly-A site or the tk-poly-A site (termination sequences are typically downstream of the polynucleotide coding sequence). Furthermore, depending on the expression system used, nucleic acid sequences encoding leader sequences capable of directing the polypeptide to a cellular compartment, or secreting it into the medium, may be added to the coding sequence of the polynucleotide of the invention; such leader sequences are well known in the art. The leader sequence(s) is (are) assembled in appropriate phase with translation, initiation and termination sequences. In one aspect, the leader sequence is capable of directing secretion of translated chimeric protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (In-vitrogene), or pSPORT1 (GIBCO BRL). Expression control sequences can be eukaryotic promoter systems in vectors capable of transforming or transfecting eukaryotic host cells; control sequences for prokaryotic hosts may also be used. Once the vector has been incorporated into the appropriate host, the host can be maintained under conditions suitable for high level expression of the nucleotide sequences; and, as desired, the collection and purification of the polypeptide of the invention may follow; see, e.g., the appended examples.

As described above, the polynucleotide of the invention can be used alone or as part of a vector (e.g., an expression vector or a recombinant virus), or in cells, to express the chimeric fusion molecules of the invention. The polynucleotides or vectors containing the DNA sequence(s) encoding any one of the chimeric fusion molecules of the invention can be introduced into the cells, which in turn produce the polypeptide of interest.

The present invention is directed to vectors, e.g., plasmids, cosmids, viruses and bacteriophages, or any expression system used conventionally in genetic engineering, that comprise a polynucleotide encoding a chimeric fusion molecule of the invention. The vector can be an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vectors of the invention into targeted cell populations. Methods which are well known to those skilled in the art can be used to construct recombinant vectors; see, for example, the techniques described in Sambrook, Molecular Cloning: A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sam brook, supra.

In a certain embodiment of the invention, endothelial cells are transduced with a recombinant virus that comprises a transgene encoding the cyclin dependent kinase inhibitor. By "transducing" is meant the introduction of exogenous nucleic acid into a cell using a recombinant virus. A recombinant virus is made by introducing appropriate viral vector sequences encoding a protein of interest into a packaging or complementing cell line. By "introducing" a nucleic acid into a cell is meant the introduction of exogenous nucleic acid into a cell by any means, including, without limitation, methods known in the art as transfection, transduction, infection, and transformation. For various techniques for manipulating mammalian cells, see Keown et al. (1990) Meth. Enzymol. 185:527-537.

By "transgene" is meant a nucleic acid sequence encoding a desired protein or polypeptide fragment operably linked to one or more regulatory sequences such that the nucleic acid sequence is transcribed and translated when the transgene is introduced into a cell, for example Tat-P14ARF, ANT-p14ARF. Transgenes typically comprise in the following order a promoter/enhancer, protein-encoding nucleic acid sequence, and polyA signal. A polycistronic transgene comprising two protein encoding nucleic acid sequences separated by an IRES sequence is also within this definition. By "regulatory sequence" is meant nucleic acid sequences, such as initiation signals, polyadenylation (polyA) signals, promoters, and enhancers which control expression of protein coding sequences with which they are operably linked. By "operably linked" is meant that the nucleic acid sequence encoding a protein of interest and transcriptional regulatory sequences are connected in such a way as to permit expression of the nucleic acid sequence when introduced into a cell. By "expression" of a nucleic acid sequence encoding a protein is meant expression of an mRNA leading to production of that protein. Where a cell is transduced with a recombinant virus containing a transgene encoding a CDKi, it will be understood that the "effective amount" of the CDKi is determined by transducing the cell with an appropriate multiplicity of infection of virus. For example, if the endothelial cell to be transduced is in vitro, standard techniques (e.g., FACS analysis) may be employed to determined the percentage of CDKi-expressing cells.

Any recombinant virus can be employed to deliver the transgene encoding the fusion protein of the invention. Preferably, the virus can transduce both dividing and non-dividing endothelial cells and confers to the transduced cell a high level of transgene expression. Thus, a variety of recombinant viruses may be engineered to encode and deliver the fusion protein of the invention to endothelial cells to inhibit angiogenesis. For example, a CDKi of the invention may be packaged in a recombinant adenovirus, a recombinant lentivirus, a recombinant retrovirus, a recombinant adeno-associated virus (AAV), a recombinant herpesvirus, a recombinant SV-40 virus, an Epstein-Barr virus, or a recombinant pox virus, such as, but not limited to, a recombinant vaccinia virus. Preferably, the recombinant virus is an adenovirus. Preferably, the adenovirus is replication-deficient. By "replication-deficient" is meant a recombinant virus that is unable to replicate in a cell other than a packaging cell. This can be accomplished, for example, when a replication-deficient adenovirus lacks a functional E1 region.

In an embodiment in which the delivery virus is a recombinant adenovirus, the adenovirus may be of any isotype. In a certain embodiment, the adenovirus lacks an essential viral protein-encoding sequence. The CDKi-encoding sequences may be inserted into one of the sequences of the adenovirus genome whose removal is not lethal. One known sequence of the adenovirus genome that may be removed is the E1 region, which controls adenovirus replication. Other non-essential regions (or combinations thereof) may also be used (e.g., the CDKi-encoding transgene may be inserted into the E2, E3, and/or E4 regions). Promoter/enhancer sequences may be constitutively active (e.g., the CMV promoter or the EF1α promoter), cell-type specific (e.g., a promoter of a VEGF-receptor gene that is specifically expressed by endothelial cells such as the VEGF-R1(Flt-1) gene promoter (GenBank Accession No.E13256) or the VEGF-R2 (Flk-1) gene promoter (GenBank Accession No. AF035121), or inducible (e.g., the cytokine-stimulated inducible nitric oxide synthase (iNOS) gene promoter). Numerous promoter/enhancer sequences are well known and their sequences available, for example, in the GenBank database (National Center for Biotechnology Information, National Institutes of Health, Bethesda, Md.). For example, the adenovirus encoding the fusion protein of the invention is replication-deficient, lacking a functional E1 region. One non-limiting way to make such a recombinant adenovirus expressing a CDKi protein is to replace the E1 region of a recombinant replication-deficient adenovirus type 5 (Ad5) vector with a CDKi-encoding transgene (e.g., a CDKi protein-encoding nucleic acid sequence operably linked to a CMV promoter/enhancer and an SV40 poly A signal). The recombinant vector is then packaged in 293 cells to produce infectious recombinant adenovirus particles.

The recombinant adenovirus encoding a CDKi of the invention may be used to transduce cells in vivo or in vitro. Such administration may be standardized by determining the multiplicity of infection (MOI) of the recombinant adenovirus, or by determining the actual number of viral particles based on the amount of viral DNA. Such standardization of viral particles is routine and is generally described in Phillipson et al., Molecular Biology of Adenoviruses, Virology Monograph, Springer Verlag, New York, N.Y., 1975.

Both amphotropic and ecotropic recombinant retroviral vectors that may be used to generate recombinant retroviral particles have been described in the art. Accordingly, a nucleic acid sequence encoding CDKi fusion protein of the invention operably linked to an appropriate regulatory sequence (e.g., a CMV promoter and/or a SV40 poly A signal) may be inserted into a retroviral vector using standard techniques. The resulting CDKi-encoding vector may then be packaged in an appropriate packaging cell line to generate recombinant retrovirus encoding a CDKi fusion protein of the invention. For a standard retrovirus, such as a Moloney murine leukemia virus (MMLV), recombinant MMLV encoding a CDKi protein of the invention may be generated. In a standard MMLV transfer vector, such as the rkat43.3 vector (Finer et al. (1994) *Blood* 83:43-50), the transgene is inserted between the gag-encoding region and the 3'LTR. A standard MMLV transfer vector has a 7 kB transgene capacity.

Where the virus is an adeno-associated virus (AAV), standard recombinant DNA techniques may be employed to generate recombinant AAV encoding a CDKi protein of the invention. Recombinant AAV can be made by transfecting a producer cell with two trans-complementing plasmids, one plasmid encoding the rep and cap proteins, and the other plasmid encoding the transgene with the AAV inverted terminal repeat (ITR) sequences. The transfected producer cell line then produces recombinant AAV infectious viral particles, which can be used to transduce cells. The transgene size capacity of an AAV transgene-ITR plasmid is typically approximately 4.5 kB. Thus, a transgene encompassing, for example, in the following or a CMV promoter/enhancer, CDKi-encoding nucleic acid sequence, IRES sequence, and SV40 polyA signal may be readily accommodated by a standard AAV transgene-ITR plasmid and may be used to generate recombinant AAV particles.

Another useful vector is the HSV based vector. Many regions of the HSV genome not needed for growth in cultured cells can be removed and a transgene encoding a fusion CDKi of the invention substituted in. Recombinant Epstein Barr viruses can also be used to deliver the CDKi of the invention to endothelial cells (see, e.g., Robertson et al. (1996) *Proc. Natl. Acad. Sci.* USA 93(21):11334-11340, and Shimizu (1996) *J. Virol.* 70(10):7260-7263).

Vaccinia viruses do not rely on the host cell's expression machinery, the inserted transgene (e.g., nucleic acid sequence encoding a ANT-p14RF fusion protein operably linked to appropriate regulatory sequences) must be flanked with the appropriate vaccinia sequences. The promoter is preferably a vaccinia virus promoter, such as H6 which is active in both early and late phases of the vaccinia virus life cycle. Additionally, after the inserted nucleic acid, a termination sequence of TTTTTNT is required in the early phase. Using homologous recombination, the vaccinia virus expression cassette, comprising a CDKi fusion protein-encoding nucleic acid sequence operably linked to regulatory sequences derived from the vaccinia virus, can be inserted into any region of the vaccinia genome which is dispensable for growth in cells (see, e.g., Perkus et al. (1989) *J. Virol.* 63:3829-3836).

It should be noted that where a recombinant virus is used to deliver the transgene encoding the CDKi of the invention, the inserted transgene may also use regulatory sequences endogenous to the virus (e.g., a viral promoter/enhancer).

In a preferred embodiment, the endothelial cell is in a mammal. In a certain embodiment, the endothelial cell is a cultured endothelial cell.

Once expressed, the chimeric fusion molecules of the present invention can be purified according to standard procedures of the art, including ammonium sulfate precipitation, affinity columns, column chromatography, gel electrophoresis and the like; see, Scopes, "Protein Purification", Springer-Verlag, N.Y. (1982). In alternative aspects, the invention is directed to substantially pure chimeric polypeptides of at least about 90% to about 95% homogeneity; between about 95% to 98% homogeneity; and about 98% to about 99% or more homogeneity; these "substantially pure" polypeptides can be used in the preparation of pharmaceuticals. Once purified, partially or to a homogeneity as desired, the polypeptides may then be used therapeutically (including extracorporeally) or in developing and performing assay procedures.

In a still further embodiment, the present invention relates to a cell containing the polynucleotide or vector of the invention, or to a host cell transformed with a polynucleotide or vector of the invention. In alternative aspects, the host/cell is a eukaryotic cell, such as a mammalian cell, particularly if therapeutic uses of the polypeptide are envisaged. Of course, yeast and prokaryotic, e.g., bacterial cells, may serve as well, in particular, if the produced polypeptide is used for non-pharmaceutical purposes, e.g., as in diagnostic tests or kits or in screening methods.

The polynucleotide or vector of the invention that is present in the host cell may either be integrated into the genome of the host cell or it may be maintained extrachromosomally, e.g., as an episome.

The term "prokaryotic" is meant to include all bacteria that can be transformed or transfected with a DNA or RNA molecules for the expression of a polypeptide of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and mammalian cells. Depending upon the host employed in a recombinant production procedure, the chimeric fusion molecules of the present invention may be glycosylated or may be non-glycosylated. Chimeric fusion molecules of the invention may also include an initial methionine amino acid residue. A polynucleotide coding for a polypeptide of the invention can be used to transform or transfect the host using any of the techniques commonly known to those of ordinary skill in the art.

In one aspect, the nucleic acids encoding the chimeric polypeptide of the invention (including those sequences in vectors, e.g., plasmid or virus) further comprise, genetically fused thereto, sequences encoding an epitope tag, e.g., an N-terminal FLAG-tag and/or a C-terminal His-tag. In one aspect, the length of the FLAG-tag is about 4 to 8 amino acids; or, is about 8 amino acids in length. Methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the polypeptide of the invention in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic non-human animals, such as mammals (e.g., mice, goats), comprising nucleic acids or cells of the invention may be used for the large scale production of the chimeric polypeptides of the invention.

In a further embodiment, the invention is directed to a process for the preparation of a polypeptide of the invention comprising cultivating a (host) cell of the invention under conditions suitable for the expression of the chimeric fusion molecule construct and isolating the polypeptide from the cell or the culture medium. The transformed hosts can be grown in fermentors and cultured according to techniques known in the art to achieve optimal cell growth. The produced constructs of the invention can then be isolated from the growth medium, cellular lysates, or cellular membrane fractions. The isolation and purification of the expressed polypeptides of the invention (e.g., microbially expressed) may be by any conventional means such as, e.g., preparative chromatographic separations and immunological separations, such as those involving the use of monoclonal or polyclonal antibodies directed against, e.g., a tag of the polypeptide of the invention or as described in the appended examples.

Depending on the host cell, renaturation techniques may be required to attain proper conformation. If necessary, point substitutions seeking to optimize binding may be made in the DNA using conventional cassette mutagenesis or other protein engineering methodology such as is disclosed herein. Preparation of the polypeptides of the invention may also be dependent on knowledge of the amino acid sequence (or corresponding DNA or RNA sequence) of bioactive proteins such as enzymes, toxins, growth factors, cell differentiation factors, receptors, anti-metabolites, hormones or various cytokines or lymphokines. Such sequences are reported in the literature and available through computerized data banks. The present invention further relates to a chimeric polypeptide, encoded by a polynucleotide of the invention or produced by the method described hereinabove and in the Examples which follow.

Liposomal delivery of the chimeric fusion protein of the invention is also within the scope of the invention. For example, the liposome comprises on its external surface a molecule that binds to a cell surface protein on the endothelial cell, wherein binding of the molecule to the cell surface protein facilitates the fusion of the endothelial cell with the liposome. Alternatively or additionally, the molecule that binds to a cell surface protein on the endothelial cell facilitates the DNA transfection of the endothelial cell by the liposome. By "external surface" of a liposome is meant the surface facing away from the interior of the liposome and, thus, away from the compartment of the liposome containing a CDKi of the invention, or a nucleic sequence encoding the same. Thus, a molecule expressed on the external surface of a liposome may be attached only to the outer leaflet of the exterior surface of the liposome, or may traverse the surface of the liposome, such that part of the molecule is expressed external to and part of the molecule is expressed internal to the liposome.

By "cell surface protein" is meant a protein that is expressed and transported to the cell surface of an endothelial cell. Such a protein may be attached only to the outer leaflet of the cell membrane of an endothelial cell (e.g., a glycosylphosphatidylinositol-anchored protein), or may traverse the cell membrane. One example of a cell surface protein on an endothelial cell is the VEGF receptor.

By "binds" is meant that the molecule on the external surface of the recombinant virus or liposome interacts with a cell surface protein on an endothelial cell such that the transgene contained by the recombinant virus or liposome is taken up by the endothelial cell.

Liposomes, which closely resemble the lipid composition of natural cell membranes, can be generated which incorporate the transgene encoding a CDKi or, alternatively, the CDKi proteins of the invention. In the latter case, the CDKi protein need not be internalizable, as the liposome will fuse to the cell membrane of an endothelial cell, thereby depositing its contents into the cytoplasm of the cell. For example, the composition may first be packaged in a liposome that bears a surface positive charge. Upon delivery to a cell either in vitro or in vivo, the liposome will fuse with the cell membrane and deposit the protein contained within the liposome into the cytoplasm of the cell. Liposome packaging and delivery of proteins is well known (see, generally, Mouritsen and Jorgensen (1998) *Pharm. Res.* 15(10):1507-1519; Selzman et al. (1999) *Circ. Res.* 84(8):867-875; and Zheng et al. (1999) *AIDS Res. Hum. Retroviruses* 15(11): 1011-1020; Fong et al. (1997) *J. Virol. Methods* 66(1):149-157.

In accordance with the invention, a nucleic acid molecule encoding a secretable chimeric fusion protein may be introduced into any cell type by any means. The cell according to this aspect of the invention includes, without limitation, a smooth muscle cell or an endothelial cell.

Fusion Proteins with Signal Sequences

In preferred embodiment of the invention, the encoded cyclin dependent kinase inhibitor is secretable. A "secretable" protein is one that is engineered such that it will be discharged or released by the cell which produces it, for example, an endothelial cell. In some applications, the fusion protein is produced in a cell following transfection of the cell with a vector encoding the fusion protein. For example, as schematically indicated in FIG. 1, endothelial cells in a tumor may be transfected with vectors that cause these cells to produce the fusion protein. In order to kill the tumor cells next to the blood vessel, the cytotoxic fusion protein must be secreted from the endothelial cells, and taken up by the neighboring tumor cells. To enable secretion of the fusion protein out of the producing cell, the fusion proteins (and the nucleic acids in the vectors that encode these proteins) can be further engineered to include a "signal sequence." The signal sequence is provided to ensure that the recombinant proteins are directed to the endoplasmic reticulum, and subsequently secreted out of the cells that produce them. Signal sequences may further be selected to direct vectorial secretion of the peptide from a particular surface of a cell, such as from the apical or basolateral surface. For example, secretion from the base of the cell can be directed using the signal sequence from urokinase. Secretion from the apical surface can be facilitated with a signal sequence, for example, from tissue plasminogen activator (TPA). In embodiments of the invention in which secretion from all surfaces is desired, the signal sequence may be derived from a protein such as alkaline phosphatase (AP).

Vectors Expressing Cytotoxic Fusion Proteins

In another aspect, the invention provides compositions and methods for expressing the fusion proteins in a cell. The invention includes expression cassettes incorporated into a vector. In some embodiments, the vector is a plasmid. An example of expression cassette elements of an expression plasmid include for example, 1) a promoter sequence to drive expression of the fusion protein, and 2) sequences encoding the fusion protein, including a signal sequence, a membrane permeability sequence or domain (MPS) and a cell cycle inhibitory sequence.

An important feature of the invention is the use of promoters that selectively express the fusion proteins in proliferating cells, and in particular, in the proliferating endothelial cells found in the blood vessels of tumors. To enhance expression of the transgene in proliferating cells, a portion of the promoter sequence from the cyclin A gene can be used to drive expression of the fusion protein.

In a preferred embodiment, expression of fusion proteins are driven by unique promoter constructs. These constructs are described in detail in the Examples which follow. Expression of the fusion proteins of the invention, are driven by unique promoter constructs combining sequences from the cyclin A gene and the endothelin gene, to provide selective expression of transgenes in proliferating cells, endothelial cells and proliferating endothelial cells.

A preferred embodiment of a promoter of the invention (designated 4×ETe/cdc6), that selectively drives expression in proliferating endothelial cells in vitro, was shown to selectively drive expression of a reporter gene in proliferating endothelial cells in two animal models of angiogenesis.

Anti-Cancer and Chimeric Fusion Molecule Cocktails

The subject chimeric fusion molecules may also be administered in combination with other anti-cancer agents, e.g., other antibodies or drugs. Also, the subject chimeric molecules or fragments may be directly or indirectly attached to an effector having therapeutic activity. Suitable effector moieties include by way of example cytokines (IL-2, TNF, interferons, colony stimulating factors, IL-1, etc.), cytotoxins (*Pseudomonas* exotoxin, ricin, abrin, etc.), radionuclides, such as $^{90}$Y, $^{131}$I, $^{111}$In, $^{125}$I among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

Administration of Compositions to Animals

For targeting a tumor cell in situ, the compositions described above may be administered to animals including human beings in any suitable formulation. For example, compositions for targeting a tumor cell may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

Formulations

While it is possible for the chimeric molecules thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration, for example, administration of the chimeric molecules to skin melanoma's include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or nonaqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

EXAMPLES

The following examples serve to illustrate the invention without limiting it thereby. It are understood that variations and modifications can be made without departing from the spirit and scope of the invention.

Materials and Methods

Plasmid Construction

Plasmid, PTRUF12 encodes for the CMV enhancer/chick β-actin promoter, beta-globin intron-exon, IRES and GFP gene. There are multiple cloning sites in between the beta-globin intron and the IRES. Another lab plasmid, p16-1003 has the alkaline phosphatase signal sequence followed by the Tat sequence and the P16 gene. The P16 gene is excised and oligonucleotides encoding exon1β of P14 and an epitope tag followed by a stop codon is ligated in its place. The epitope tag is the hemaglutinin tag (YPYDVDPDYA) (SEQ ID NO: 6)). Two antibodies to FLAG tag showed multiple bands on western blots for the glioma cell lines. The gene are then excised from the p16-1003 plasmid and cloned into the PTRUF12 between the globin intron and IRES. The PTRUF12 also contains AAV ITRs.

Plasmid DNA: Two commercially available reporter plasmids, GWIZ GFP and GWIZ alkaline phosphatase, are used to determine the % transfected cells and quantify gene expression, respectively. Plasmids are isolated using a modified column procedure. Bacteria are grown in 2 L shaker flasks overnight. They are collected by centrifugation and resuspended in resuspension buffer (50 mM Tris; 10 mM EDTA, pH 8). Bacteria are lysed with alkaline lysis buffer (0.2M NaOH, 1% SDS) and neutralized with neutralization buffer (1M KAc, 7M $NH_4Ac$). Cell lysate is centrifuged and supernatant is clarified by filtration. Filtrate is loaded onto a TMAE column equilibrated with 0.6M NaCl and washed until $OD_{260}$ returns to baseline. Plasmid is eluted with 2M $(NH_4)_2SO_4$ in 1×TE. Plasmid containing fractions are pooled and applied to an octyl-sepharose column equilibrated with 1.6M $(NH_4)_2SO4$ in 1×TE. This flow through column removes endotoxin and RNA. Fractions are pooled and dialyzed against TE. 2 Ls of DH5-α yields 4 to 10 mg of plasmid.

A fragment of the cyclin A promoter spanning the region −215 to +100 (Henglein et al., Proc Natl Acad Sci 91:5490-5494, 1994) was isolated from human genomic DNA (Promega) using PCR and published primer sequences. The fragment created by the primers, i.e., (5'-GCGTCGGGC-CCTAAATCC-3' (SEQ ID NO:7)) and (5'-CCCAGCTC-GAGACCACGC-3' (SEQ ID NO:8)), was ligated into plasmid vector pCR2.1 (Invitrogen), to create plasmid pCA1135. The cyclin A promoter was isolated from a SacI fragment from a cloning plasmid and ligated into a plasmid backbone containing either the luciferase (pLC1154) or chloramphenicol acetyl transferase (CAT) expression cassette plasmids.

A fragment of the cdc6 promoter spanning the region from −130 to +7 (Williams et al, *Proc Natl Acad Sci* 94:142-147, 1997; Yan et al., *Proc Natl Acad Sci* 95:3603-3608, 1998) was constructed from two sets of oligonucleotides. Two sets of oligonucleotides were designed with the addition of a 5' SacI- and 3' BsmBI-compatible overhangs. Once annealed and ligated, the Cdc6 promoter was inserted into a GENEMEDICINE plasmid backbone to drive the expression of luciferase (pLC1284) or chloamphenicol acetyl transferase (pCT1330) reporter genes.

The mouse endothelin enhancer from −364 to −320 (Bu and Quertermous, *J Biol Chem* 272:32613-22, 1997) was synthesized using oligonucleotides, and annealed to produce a double-stranded 50-bp DNA fragment with 5' BglII- and 3' BamHI-compatible overhangs. The fragment was multimerized by ligation at high concentration and digested with BamHI and Bgl II to eliminate head-to-head and tail-to-tail ligation products. The species containing four tandem copies was gel purified and inserted into a BamHI site upstream of the cyclin A and cdc6 promoters.

Figure 4:
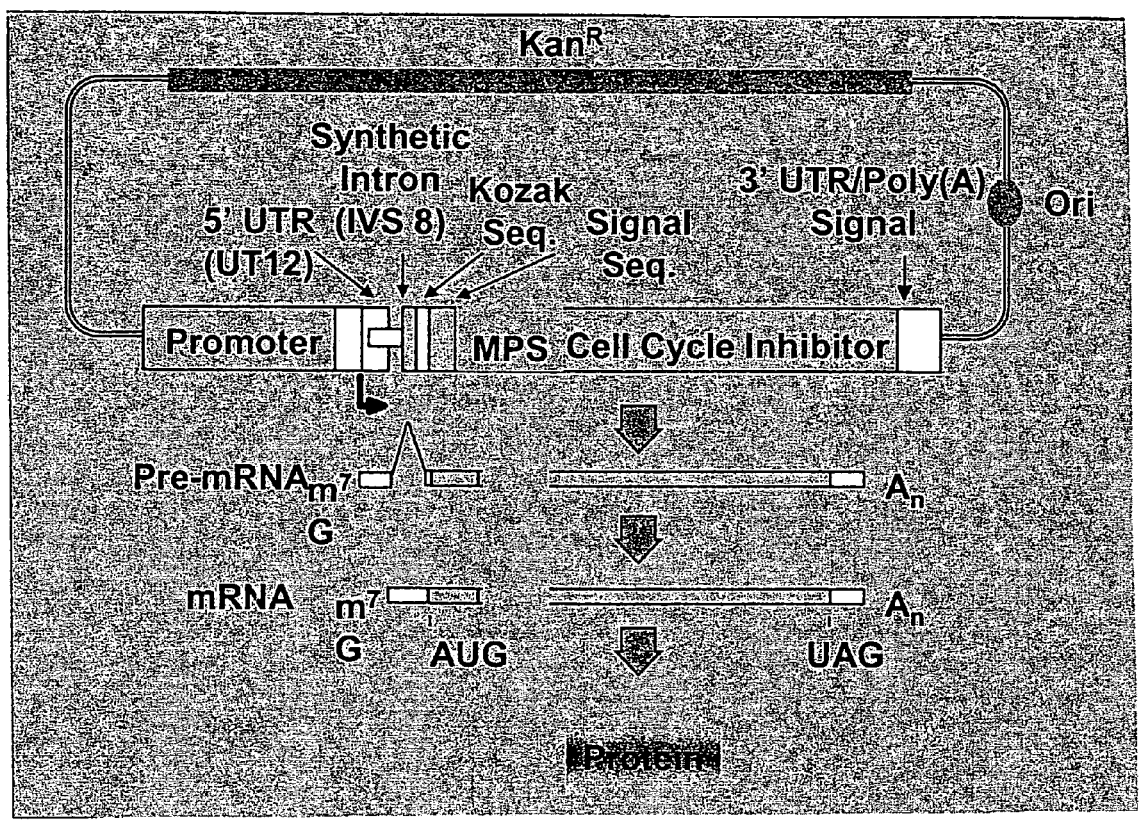
FIG. 4 is a schematic diagram showing components of a cytotoxic fusion protein construct.
Figure 6:
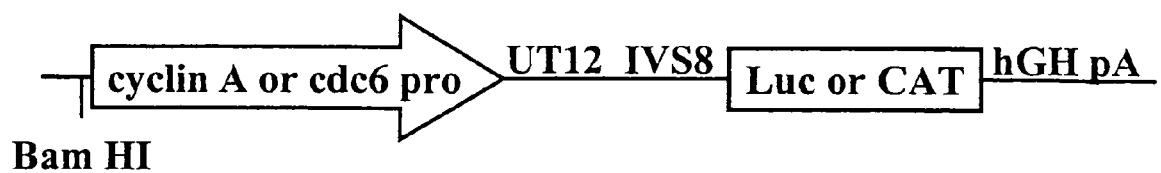
FIG. 6 is a schematic diagram showing the design of promoter constructs of the invention that selectively drive transgene expression in proliferating cells using sequences from cyclin A or cdc6 genes.

Within the constructs, the cyclin A or cdc6 promoter element was fused to UT12, a modified 5' untranslated region from the CMV immediate early gene, and IVS8, a synthetic intron. The reporter gene was either luciferase or CAT, and the 3' untranslated region and poly A site were from the human growth hormone gene (Blezinger et al, *Hum Gene Ther* 10:723-731,1999). FIGS. 4 and 6 are schematic diagrams showing the design of the vector constructs.

Promoter Construction

Cdc6 Promoter Construction: A fragment of the cdc6 promoter spanning from region −130 to +7 was constructed from two sets of oligos. Two sets of oligos were designed with the addition of a 5' SacI- and 3' BsmBI-compatible overhangs. Once annealed and ligated, the cdc6 promoter was inserted into a plasmid backbone to drive the expression of luciferase (pLC1284) or chloramphenicol acetyl transferase (pCT1330) reporter gene expression. The luciferase gene is excised by restriction digest and the CDKI gene is inserted using the Hind III/Nco I. Plasmid is sequenced both from clone and any large preparation. Because of the multimerized endothelin enhancer, the plasmid must be propagated in Stbl2 competent cells. Clones and plasmid isolated from large cultures are routinely screened for intact endothelin enhancer.

Construction of rat Endothelin Enhancer/human cdc6 Promoter: A fragment of the cdc6 promoter spanning from region −130 to +7 is constructed from two sets of oligos. Two sets of oligos are designed with the addition of a 5' SacI- and 3' BsmBI-compatible overhangs. Once annealed and ligated, the cdc6 promoter will replace the CMV promoter in the membrane form of alkaline phosphatase expression plasmid just upstream of the transcription initiation site. The mouse endothelin enhancer from −364 to −320 (Bu and Quertermous, 1997) is synthesized on oligonucleotides, and annealed to produce a double-stranded 50-bp DNA fragment with 5' BglII- and 3' BamHI-compatible overhangs:

gatctGTACTTCATACTTTTCATTCCAATGGGGTGACTTTGCTTCTGGAG
(SEQ ID NO: 9)

aCATGAAGTATGAAAAGTAAGGTTACCCCACTGAAACGAAGACCTCctag
(SEQ ID NO: 10)

The fragment is multimerized by ligation at high concentration and digested with BamH I and Bgl II to eliminate head-to-head and tail-to-tail ligation products. The species containing four tandem copies is gel purified and inserted into a BamHI site upstream of the cdc6 promoter (pTat-CDKI 1001).

Signal Sequence

The alkaline phosphatase signal in pTat-CDKI is excised using Hind III/BamH I. Oligos encoding for the following signal sequences are ligated in its place:

```
GDNF
MKLWDVVAVCLVLLHTA-           pTat-CDKI-1002
(SEQ ID NO: 11)

IGFBP3
MQRARPTLWAAALTLLVLLRGPPVARA  pTat-CDKI 1003
(SEQ ID NO: 12)

Urokinase
MRALLARLLLCVLVVSDSKG         pTat-CDKI-1004
(SEQ ID NO: 13)

Growth Hormone
MATGSRTSLLLAFGLLCLPWLQEGSAFPTI  pTat-CDKI-1005
(SEQ ID NO: 14)
```

All sequences are confirmed before any further experimentation. Expression is tested under a CMV promoter because the endothelial cells should be confluent to become polarized. Polarized secretion will not be tested until the cells become polarized. Hence, a constituitive promoter is used for these studies. Successful candidate signal sequences are ligated into $ET_c$/cdc6 promoter expression plasmids for organ culture and in vivo gene transfer studies.

Lipopeptide Synthesis:

Peptides are synthesized and HPLC purified by the University of Florida ICBR Core Facility. DSPE-PEG(2000)-COOH is purchased from Avanti Polar Lipids (Alabaster, Ala.) and dissolved in 0.5 ml of dichloromethane (DCM) and diluted with 4 ml of dimethylformamide (DMF). Solid carbonyldimidazole (CDI) is added at 3 molar excess and the carboxyl group of DSPE-PEG(2000)-COOH is activated by stirring under nitrogen for 1 hour at room temperature. The peptide (2 molar excess over DSPE-PEG(2000)-COOH) is dissolved in 0.5 ml DMF and then added to the activated DSPE-PEG(2000)-COOH. Ten ml of re-distilled triethylamine is added and coupling allowed to proceed overnight under nitrogen at room temperature. The solvent is evaporated to dryness and the residue further dried overnight under vacuum. The dried residue is re-dissolved in about 10 ml of water and the solution adjusted to pH 7 using 1N sodium hydroxide. The peptide-DSPE-PEG(2000) conjugates are then purified by reverse phase HPLC using a Vydac C4 column and 5 mM ammonium phosphate, pH 7/acetonitrile solvent system. Fractions containing pure conjugates are pooled and then lyophilized. Molecular composition is confirmed by mass spectrometry.

Cationic Lipid/Plasmid DNA Complex (Lipoplex)

The cationic lipid 3β-[N-(N',N'-Dimethylaminoethane)-Carbamoyl]Cholesterol (DC-Chol) (Avanti Polar Lipids, Inc.) is mixed with the helper lipid 1,2-Dioleoyl-sn-Glycero-3-Phosphoethanolamine (DOPE) in molar ratios of 1:1 and 3:2, respectively. The lipids are mixed in chloroform/methanol and then dried under argon gas to form a thin layer. The film are hydrated with a 40% ethanol, 5% dextrose solution to form micelle suspension. The suspension was mixed with plasmid DNA at N/P ratio of 4:1 and 5:1 respectively. It is at this time that the DSPE-PEG-Peptide are added to the lipid/DNA suspension. The suspensions are dried using a vacuum and then re-hydrated in sterile water, yielding a final DNA concentration of 0.2 mg/ml. Particle size distribution are determined using a NICOMP 380 ZLS (PSS NICOMP, Santa Barbara, Calif.). Previous results showed DC-Chol lipoplexes to have an average diameter of 70 nm. For fluorescent labeled transfection complexes, 5 mol % 1,2-Dioleoyl-sn-Glycero-3-Phosphoethanolamine-N-(7-Nitro-2-1,3-Benzoxadiazol-4-yl) (NBD-DOPE) or 0.5 mol % 1,2-Dioleoyl-sn-Glycero-3-phosphoethanolamine-N-(Lissamine Rhodamine B Sulfonyl) (Rhodamine-DOPE) (Avanti Polar lipids, Inc.) are added to each cationic lipid mixture in chloroform then dried under argon.

HBMEC Cell Culture:

HBMECs are purchased from Cell Systems, Inc. (Kirkland, Wash.). The cells were seeded onto attachment factor-coated culture plates and maintained in CSC-complete medium according to the protocol of the manufacturer. For up regulation of CXCR4, VEGFR and FGFR, HBMECs are grown subconfluently onto attachment factor-coated 100-mm dishes. The cells are starved in 0.5% FBS containing serum-free CSC medium for 4 h and then stimulated with 30 ng/ml VEGF for 5 h. Recombinant human SDF-1, recombinant human VEGF, and recombinant human bFGF are purchased from Pepro Tech (Rocky Hill, N.J.). Antibodies to each of the receptors are purchased from R & D Systems, Minneapolis, Minn., PharMingen, San Diego, Calif., and Abcam, Cambridge, United Kingdom. Expression of each of the receptors are verified by FACS using standard labeling procedures with appropriate primary and fluorescent secondary antibodies.

Cell Adhesion and Inhibition Assay

A cell adhesion and inhibition assay is used to evaluate the binding affinity of the $\alpha_v\beta_3$ binding peptides. HBMECs (2×104 cells per tube) are preincubated with the CDMRGD-MFC targeted lipoplexes and non-targeted lipoplexes at (0 to 5 mg of plasmid DNA) at 370 C. for 30 minutes in suspension and transferred onto vitronectin coated 96-well microtiter Immulon-2 plates (Dynatech Laboratories Inc., Chantilly, Va.). After 90 minutes of incubation at 37° C., the number of live cells are measured at 450 nm absorbency by adding WST-1 proliferation reagent (Boehringer Mannheim, Indianapolis, Ind.) for 1 hr.

Arterial Blood Vessel Organ Culture:

Rats are anesthetized by an intraperitoneal injection of pentobarbital sodium (160 mg/kg) and killed by decapitation. The brain is removed and placed in an ice-cold oxygenated physiological cerebrospinal fluid (pCSF, see below for composition). Posterior cerebral arteries are isolated and mounted in an arteriograph. The arteriograph is placed on an inverted microscope and the artery is visualized with a monochrome CCD camera coupled to a calibrated video caliper system to measure arterial diameter. The arteries are slowly pressurized to 70 mmHg under no flow conditions using a pressure servo-null system (Living Systems Inc., Burlington Vt.), and warmed to 37° C. while being continuously superfused (5 ml/min) with pCSF bubbled with 21% O2, 5% CO2, 74% N2 (pH 7.35-7.40 in the bath). After an equilibration period of about 20 minutes at 70 mmHg, arteries show stable myogenic tone. The response to pressure, 60 mM and 16 mM Potassium are used as benchmarks for interexperiment normalization and to ensure artery health. In some experiments, the arterial segments were denuded of endothelium by passing an air bubble through the lumen.

Implantation of RG2 Tumors:

A master cell bank of RG2 cells was created, such that freshly thawed cells are used for each set of tumor implantations. For large experiments requiring all day implantations, cells are in serum free media under dilute conditions and concentrated by centrifugation for every 6 rats. Male adult Fischer 344 rats (175-200 gm) are anesthetized with 2% isofluorane. After a midline incision, the periosteum are displaced, and a burr hole are drilled into the right cerebral cortex. A 2-ul suspension of $5 \times 10^4$ RG2 cells in DMEM, minus serum or antibiotic, is injected-into the hole by stereotactic injection.

Intracarotid Administration of Transfection Complexes:

Rats are anesthetized with 2% isofluorane administered using an anesthesia instrument. A silicone catheter (Helix Medical) is implanted into the carotid artery and tied off distally for cranial administration. The external carotid artery is tied of to insure that all injected material is diverted to the internal carotid artery. The catheter are exteriorized between the shoulder blades and exit through a hole in the back of the neck. The catheter are filled with heparin solution (10 units/ml) and sealed with stylets. A syringe containing the transfection complexes are fitted into an infusion pump and attached to the catheter. Transfection complexes are administered to the rat requiring no anesthesia at an injection rate of 0.1 ml/min. Growth studies have shown that the installation of the catheter has no effect on tumor growth rate.

Plasmid Extraction from Tissues and Quantification:

Plasmid DNA from lungs and brain tissue are digested by incubation with digestion buffer (100 mM NaCl, 10 mM Tris-HCl, [pH 8.0], 25 mM EDTA [pH 8.0], 0.5% SDS, and proteinase K [0.1 mg/ml]) at 500 C. The samples are extracted with an equal volume of Tris-buffered phenol (pH 8.0), followed by extraction with chloroform:isoamyl alcohol (24:1, v/v) and ethanol precipitation. The DNA precipitates are dissolved in TE buffer (10 mM Tris [pH 7.5], 1 mM EDTA), and DNA concentration are measured by UV absorption at 260 nm. A polymerase chain reaction (PCR) assay using Taqman PCR (Perkin-Elmer, Foster City, Calif.) are used to quantify the amount of plasmid DNA associated with the tissue or cell extract. The primers used in the reaction are a forward primer, 5'-GCC GTA ATA TCC AGC TGA ACG-3' (SEQ ID NO: 15) which primes in the CMV 5' untranslated region (UTR), and a reverse primer, 5'-(FAM)GCA AGT CGA CCT ATA ATG CCG(TAMRA)-3' (SEQ ID NO: 16), which primes in the CAT coding region. The probe sequence is 5'-CCA GCC TCC GGA CTC TAG AGG A-3' (SEQ ID NO: 17). The initial copy numbers of unknown samples are determined by using an Applied Biosystem 7700 sequence detector to compare them with a standard curve generated from purified pCMV-CAT of known initial copy numbers.

Tissue Homogenates for Assay of Alkaline Phosphatase Activity:

Tissues are weighed, flash frozen in liquid nitrogen and stored at −80° C. Tissues are thawed and homogenized in AP-lysis buffer, 250 mM Tris (pH 7.4), 1% TX-100, 0.1 mM PMSF with a tissue homogenizer at a concentration of 100 mg tissue/ml of lysis buffer. The homogenates are heat inactivated at 65° C. for 30 minutes. Samples are centrifuged in a microcentrifuge and 300 μls of supernatant are added to the anti-AP coated 96 well plates. After overnight incubation, wells are washed, alkaline phosphatase substrate are added and assayed using a microtiterplate reader.

Perfusion and Tissue Processing for Histology

Animals are deeply anesthetized an approved anesthetic and perfused through the ascending aorta with 50 ml of isotonic saline, followed by 250 ml of ice cold 4% PFA in 0.1M phosphate buffer (PB, pH 7.4). Brains are then removed and post-fixed for two hours in the same solution. The brains are then transferred to 20% sucrose in 0.1M PBS for cryoprotection. Five series of 40 μm thick coronal sections are cut on a freezing stage sliding microtome.

Immunohistochemistry:

The free-floating sections are rinsed three times in potassium-phosphate buffer (KPBS), quenched for 10 min in 3% $H_2O_2$/10% methanol in KPBS. The sections are mounted on chrome-alum coated slides and preincubated with 5% normal horse serum (NHS)/0.25% Triton X-100 in KPBS and incubated overnight at room temperature with 1:2000 dilution anti-GFP antibody, anti-HA antibody, anti-CXCR4 antibody, anti-FGFR antibody, anti-VEGFR antibody, or anti-$\alpha_v\beta_3$ antibody in 2% NHS/0.25% Triton X-100 in KPBS in humidity saturated chamber. This treatment is followed by incubations with 1:200 dilution of biotinylated horse anti-mouse antibody (BA2001, Jackson Laboratories) in 2% NHS/0.25% Triton X-100 in KPBS and then avidin-biotin-peroxidase complex (ABC, Vector). The reaction is visualized using 3,3-diaminobenzidine as a chromogen. Sections are dehydrated in ascending alcohol concentrations, cleared in xylene and coverslipped in DPX. The same general procedure 1 is followed for all primary antigens mentioned in this grant. (this is for mouse monoclonals, for rabbit polyclonals the secondary is a goat anti-rabbit using NGS as blocking agent).

Alternatively, antibody staining for each of the constructs and GFP is used to show that the peptide is able to enter non-transfected cells. For these studies, cells are plated out on chambered covered slips. Cells are detergent permeabilized, fixed, incubated with primary antibody followed by Rhodamine labeled goat anti-mouse. The endogenous GFP fluorescence are used to identify transfected cells. If the signal is too weak, a rabbit polyclonal is incubated with the cells followed by a fluorescein labeled goat anti-rabbit secondary antibody.

Cell Transfection

A172, T98G and RG2 cells are plated in 6 well plates. Each cell line is tested separately with all plasmids. Plasmids are transfected into cells using a commercially available transfection reagent. Cells are monitored for GFP fluorescence to ensure transfection. Aliquots of cell supernatant are harvested at 24 and 48 hours after transfection. At 48 hrs, cells are harvested, lysed under conditions that release all proteins from ER and golgi and centrifuged. Cell pellets and supernatants are analyzed by Western blot for peptides using anti-HA (Santa Cruz Biotechnology, Santa Cruz, Calif.). A modified 18%-24% discontinuous gradient gel yields excellent resolution of low molecular weight peptides.

Plasmid DNA Mediated Cell Killing

Each cell line is tested for cell killing activity. Conditions include the Tat-rExon1, rExon1-Tat, ANT-rExon1, rExon1-ANT, Tat, ANT and Exon 1. The most active construct is also tested without the signal sequence. Cells are plated at 40% confluency on 6 well plates. Each of the fusion peptides are tested in a plasmid DNA dose response. Cell killing can be evaluated in two ways. The first is to harvest the cells 48 to 72 hours after transfection and assay for % viable cells by FACS. This can be further fine tuned by including the IRES-GFP downstream of the fusion peptide. FACS analysis can then gate on both GFP positive cells and the cell viability. By correlating the percent of viable cells with the number of GFP positive cells, a better measure of the bystander effect can be obtained.

Western Blot Cells are plated in 6 well plates at 50% confluency (approximately $5 \times 10^5$ cells). A172, T98G, RG2 cells and human brain vascular endothelial cells (HBMECs obtained from Cell Systems, Kirkland, Wash.) are transfected with 5 µg of plasmid DNA formulated with DMRIE-C (InVitrogen, Inc.) in 1 ml in serum free media for 4 hours. Transfection media is replaced with complete media and cells are grown for 24 to 48 hours depending on the cell type. Cells are removed from the plate and centrifuged. Cell pellets are solubilized in lysis buffer (200 mM Tris, 100 mM NaCl, 1% NP-40, 0.5% Deoxycholate, 0.1% SDS, 1.2 mM EDTA, 1 mM $Na_3VO_4$, 50 mM NaF, 2 mM DTT, 1 mM AEBSF, Leupeptin, Pepstatin A, Aprotinin, 1.5 ng/ml each. Cell lysate is cleared by centrifugation. Cell lysate and cell supernatant are diluted 1:1 with loading buffer, boiled for 5 minutes and loaded onto a denaturing 18%/24% discontinuous polyacrylamide gel. After electrophoresis, proteins are electroblotted onto transfer membrane. Transfer membrane is blocked overnight with 10% non-fat milk in TBST, 0.5% tween. After rinsing with TBST, transfer is incubated with primary antibody against HA (Santa Cruz Biochem., Santa Cruz, Calif.) for 2 hrs at room temp. After thoroughly washing, rabbit anti-mouse cross-linked to horse radish peroxidase is incubated with the transfer membrane for 2 hrs. After thoroughly washing the transfer membrane with TBST. The transfer membrane is incubated with ECL reagent (Amersham Biosciences), wrapped in plastic wrap, placed into an X-Ray file cassette with film and exposed for 10 to 60 seconds. Films are then developed.

Cytotoxicity Assay

RG2 cells and HBMECs are plated in 6 well plates 24 hours before transfection at a sufficient density to allow for two cell doublings. Cells are transfected with plasmids in serum free media for 4 hours. Transfection media is replaced with complete media and cultures continue for two doubling periods. Cells are removed by trypsinization and counted in a coulter counter. Cell viability is determined by trypan blue staining and cell counting. Alternatively, a 96 well plate assay can be used and cell viability measured using an MTT assay.

Table 1 Listing of Receptors, Ligands and Receptor Binding Peptides for Targeting of Lipoplexes Endothelial Cells

| Receptor | Ligand | Peptide Sequence |
|---|---|---|
| CXCR4 | SDF-1 | RRNalCYCitKdEPYRCitCR* (SEQ ID NO: 18) |
| Flt-1 (High Affinity $VEGF_R$) | VEGF | NGYEIEWYSWVTHGMY (SEQ ID NO: 19) |
| KDR/FLK-1 (low affinity $VEGF_R$) | VEGF | HTMYYHHYQHHL (SEQ ID NO: 20) |
| $FGF_R$ | bFGF | MQLPLAT (SEQ ID NO: 21) |
| $\alpha_v\beta_3$ | Vitronectin | CDMRGDMFC** (SEQ ID NO: 22) |

*Nal = L-3-(2-naphthyl) alanine, Cit = L-citrulline
**Peptide sequence from appendix manuscript Example 1

In Vitro Cell Binding Assay

DC-Chol/DOPE lipoplexes are prepared containing each of the peptides listed in Table 1 as a DSPE-PEG-peptide and also containing a 0.5 mol % NBD-DOPE. Either the GFP or alkaline phosphatase expressing plasmid are used to form the lipoplexes. The mol % of lipopeptide is titrated from 0 mol % to 10 mol %. Binding is tested at 0.5 µg, 1 µg, 2.5 µg and 5 µg of plasmid DNA. HBMECs are plated at 50% confluency in cell well plates the night before. Lipoplexes are added to the cells and incubated for 1 hour. Binding is done in the presence and absence of serum, the purpose being to control for any inhibitory components in the serum. Cells are washed 5× with PBS and either media is replaced for fluorescence microscopy or cells are removed from the plate, solubilized with 1% TX-100 and cell associated fluorescence is measured to measure the amount of bound lipoplex. Demonstration of receptor binding specificity is conducted by incubating peptide-lipoplex at optimal peptide surface density and DNA concentration. Native ligand is titrated into the incubation to determine $IC_{50}$. Binding specificity for the CDMRGDMFC targeted lipoplexes is tested using the cell adhesion inhibition assay. One additional control includes lipoplexes with DSPE-PEG alone with no peptide at the same mol % as the peptide-PEG-DSPE. This provides a better measurement of binding specificity because the PEG should reduce non-specific binding of the lipoplexes to the cells.

Each of the peptides show increased binding specificity as the mol % is increased. Saturation occurs between 5 and 10 mol %. Saturation of binding occurs between 2.5 and 5 µg of plasmid DNA. A ten fold higher concentration of native ligand inhibits lipoplex binding to cells. A preincubation of the ligand with the cells prior to addition of peptide-lipoplex can also be conducted for effective inhibition. Titration curves are obtained, especially for where mixtures of multiple peptides are tested. The predicted order of binding affinities for peptide targeted lipoplexes are as follows: CXCR4<FGFR<$\alpha_v\beta_3$<KDR/Flk-1<Flt-1. This is based on the following information. The CXCR4 peptide has an $IC_{50}$ in the nM range for inhibiting HIV, the implication being that this is a direct correlate of the peptide binding affinity to its receptor. The FGFR peptide when displayed on phage showed high binding affinity of phage to FGFR expressing cells (KD~10-10M). The $\alpha_v\beta_3$ integrin binding peptide has a 10 µM $IC_{50}$ for inhibiting HUVEC attachment to vitronectin coated plates. The Flk-1 and Flt-1 binding peptides have $IC_{50}$ in the 100 µM range. However, VEGF 165 binds to Flk-1 at a 10 fold less saturating concentration than Flt-1, hence, Flt-1 will have the lower degree of binding.

Example 2

Other Crosslinking Agents

Other crosslinking chemistries can be implemented, such as EDC/NHS or incorporation of an additional cysteine at the N-term or C-term. For peptides with an internal disulfide bride, the peptide can be coupled to the column. Cyclization can be done while the peptide is still on the attached to the support and cleavage of the peptide from the support yields the free thiol to react with a malimide at the end of the DSPE-PEG. The peptide may not be accessible to bind to the receptor because it is buried in the PEG. If this is observed, peptides are derivatized to succinyl-DOPE and tested for binding. There are other smaller molecular weight lipids, besides PEG-PE phospholipids that can be used to shield the surface charge of the lipoplexes, such as gangliosides, GM1 or palmitoylglucuronide47.

Example 3

Expression of Peptide Targeted Lipoplexes

Cells are incubated for 24 to 48 hours after addition of lipoplexes to measure expression of transgenes. The percent transfected cells are quantified by expressing GFP and quantifying the percent transfected cells using FACS. Expression is quantified by expressing alkaline phosphatase and measuring the amount of human placental alkaline phosphatase in the tissue culture media. This enzyme is heat stable and all other phosphatases are inactivated by heating the supernatant to 65° C. for 30 minutes. The supernatant is clarified by centrifugation and activity is measured using a chemiluminescence assay (SIGMA).

The expression results should parallel the binding results. There should also be a correlation between the number of transfected cells and the amount of transgene being expressed. Based on previous experience with incorporation of lipopeptides into lipoplexes, there should be no effect the ability of the lipoplex to transfect cells. If anything, expression should increase because the peptides will trigger receptor mediated endocytosis. Induction of endocytosis should be observed in the binding studies where the peptide targeted lipoplexes are fluorescently labeled and cell interactions are followed by fluorescence microscopy. To test for any PEG interfering with cell entry or unpackaging, the peptide is derivatized to succinyl-PE (lacking the PEG), incorporating it into the lipoplexes and testing for gene expression.

Example 4

Peptide Targeted Lipoplexes to Vascular Endothelial Cells

Blood vessels are pretreated with VEGF, FGF or SDF-1 and upregulation of receptors are verified by antibody staining. Peptide targeted lipoplexes are tested individually. The surface density is at 10 mol % and the amount of plasmid DNA varies from 1 µg/ml to 15 µg/ml with a minimum of 4 doses tested. The concentration corresponds to approximately a 25 µg to 300 µg plasmid dose administered intravenously. The flow rate is about 1 ml/min. The rates can fluctuate between 0.5 ml to 9 ml/min. Transfection complexes are fluorescently labeled and binding is followed by fluorescence microscopy using an inverted microscope. The transfection complexes are recycled through the vessels until no further increase in cell fluorescence is observed. Once saturation is reached, vessels are flushed and viewed for intracellular internalization of the lipoplexes. Competition studies comprise a pre-perfusion of native ligand followed by the administration of the transfection complexes, because this will represent the conditions in the proliferating tumor blood vessels. Quantitation of the amount bound is determined by measuring the amount of cell associated fluorescence. If there is insufficient signal, plasmid DNA is extracted from the vessels and quantified by qPCR (see Plasmid Extraction from Tissues and Quantification infra). These studies are also performed in unstimulated vessels where the resting surface density for each of these receptors is low. This provides information on transfection complex binding to normal endothelium.

Once optimal plasmid dose and binding affinity are determined for each of the peptides, the effect of two different peptides is tested. The selection of peptides combined and the ratios are based on receptor density, the degree of non-specific interactions with unactivated endothelium, and the binding affinity of the peptide lipoplexes based on the inhibition titration curves. For example, if CXCR4 and KDR/Flk-1 have similar receptor densities and the binding affinities are observed in the organ culture. The ratios can be varied depending upon the binding affinities. For example, Flt-1/CXCR4: 90/10, 80/20, 75/25, 50/50 and 25/75. The surface density of the total lipopeptide is held constant at 10 mol %, and % binding are measured as a function of plasmid dose. The ratio that yields the highest degree of binding is used for competition assays with each of the native ligands separately.

Expression of the peptides is followed by GFP expression. For these studies, rhodamine labeled peptide-lipoplexes are used to follow lipoplex binding. GFP expression is visualized by fluorescence microscopy. Testing conditions are the same as those used for the binding studies. Both the high affinity and low affinity peptide-lipoplexes by themselves and the optimal ratio of the low affinity and high affinity receptors are tested. Included is a non-targeted transfection complex. For competition, the native ligand is used with each of the corresponding peptide-lipoplexes. The stage of the organ culture can be removed after binding and internalization have been completed, and placed in a $CO_2$ incubator. Cultures can be viewed with the fluorescent microscope periodically for GFP expression. Viability of the cultures are checked by a propidium iodide stain. Functionality is checked by measuring the response to endothelial vasodilation, smooth muscle cell dilation and contraction.

Example 5

Optimized Peptide Targeted Lipoplex in Rat Brain Tumor Model

Prior to initiation of the injection of lipoplexes, the brain tumors generated from RG2 cells are tested for expression of all the targeting receptors by immunohistochemical staining. RG2 cells (approximately $5 \times 10^4$) are stereotactically implanted into the right striatum on day 0. 7 days later, carotid arteries are catheterized and the peptide lipoplexes are administered the next day via the catheter. Catheters are placed in such a way that anesthesia is not required during lipoplex administration. The peptide-lipoplexes yielding the lowest binding affinity, the highest binding affinity and the optimal ratio of the low and high affinity peptides determined from the arteriographs are tested for plasmid biodistribution following intracarotid artery administration. A non-peptide lipoplex is also tested for comparison of selective binding. Biodistribution is measured at three plasmid doses, 50, 100 and 200 µg administered through an infusion pump at 100 µl/min. There is an n=3 per plasmid dose plus another set of animals to determine background levels for the qPCR. Two hours after completion of the infusion rats are euthanized, liver, spleen, lung and brain are harvested, plasmid DNA is extracted and quantified by qPCR. The selectivity index is determined by: (Peptide-Targeted Lipoplex$_{tissue}$/Non-Targeted Lipoplex$_{tissue}$) for each of the plasmid doses. This is determined for all the tissues. The plasmid dose that yields the lowest selectivity index to the non-targeted tissue and the highest selectivity index to the brain is tested for histochemical analysis of binding. The peptide-lipoplex by itself and co-administered with the competing native ligand, and the non-targeted lipoplex is administered to tumor bearing rats. Two hours after infusion is completed, rats are euthanized and perfused with fixative and processed for histochemistry. Sections are counterstained with an endothelial cell marker such as Factor VIII to view co-localization of lipoplexes in endothelial cells. DAPI is also used to visualize all cells by staining the nuclei.

Expression experiments are performed at the same time as the biodistribution studies. The GFP expression plasmid is used for showing expression. The same conditions are used. There is an n=3 per treatment group and plasmid dose. There is also an untreated group to control for autofluorescence. Sections are stained with anti-GFP and a morphometric microscope is used to reconstruct the 3-dimensional expression area in the brains. Endothelial cells are identified by markers such as Factor VIII/VonWillebrand factor.

Example 6

Polarized Expression of Tat-CDKI-HA

Endothelial cells are plated at 50% confluency and transfected the next day. The pTat-CDKI, 1001, 1002, 1003, 1004 and 1005 are tested for polarized secretion. Once the cells reach concluency, they are polarized. This is checked by adding dye to the upper chamber of the transwell. Media from the upper and lower chamber are sampled throughout the time course and assayed for preferential distribution of the HA tagged gene product.

Example 7

Effect of Fusion Proteins on Tumor Cell Viability In Vitro

Fusion proteins containing a Tat domain and a p16 domain were synthesized as peptides. Two forms of the peptides were made, one with Tat on the amino terminus (designated Tat-P16), and the other with p16 on the amino terminus (P16-Tat). Control peptides were synthesized having only the Tat or P16 sequence. The peptides were incubated with A172 glioblastoma cells, then the cells were assayed for viability. Results using fluorescently labeled peptides showed that the peptides entered the cells, and after 30 minutes of incubation at 37° C. with Tat-P16 peptides (6 µM concentration), the cells began to round up and subsequently die.

Other experiments were performed using two glioma cell lines, i.e., T98G and RG2. 1×10$^6$ cells per well were incubated in 6-well plates with peptides in complete media for 1 hr. Cells were removed from the plate using a cell stripper and the percentage of viable cells was determined by staining with propidium iodide and analyzing by fluorescence activated cell sorting (FACS).

Table 2 shows the cytotoxic effect of the Tat-P16 peptide on two glioma cell lines, i.e., T98G and RG2. As can be seen from the table, the MPS (Tat alone) was ineffective for cell killing. After incubation with P16 alone, 93% of the T98G cells, and 78% of the RG2 cells were still viable. In contrast, only 35% and 39%, respectively, of the two cell types were alive after incubation with Tat-P16. This result demonstrated that the Tat-P16 peptide was able to cross the cell membrane, and effect inhibition of the cell cycle in a large percentage of the cells in both glioma cell lines.

TABLE 2

| Peptide | T98G Cells % Viable Cells | ST Dev | RG2 Cells % Viable | St Dev |
|---|---|---|---|---|
| Tat-P16 | 35.16 | 3.50 | 39.04 | 1.60 |
| Tat | 94.93 | 0.86 | 93.99 | 1.60 |
| P16 | 93.42 | 1.93 | 77.68 | 3.93 |

Other assays were performed, as described above, in which the cell killing efficacy of the Tat-P16 and P16-Tat peptides was compared. Similar results were obtained using peptides having the P16 sequences (either rat or human) on either end of the molecules. These studies demonstrated that the domain position in the peptide was not critical in determining cell membrane translocation, or effective interaction of the cytotoxic domain with its intracellular target.

Example 8

Uptake of Cytotoxic Fusion Proteins by Intact Blood Vessels

Figure 5:
FIG. 5 is a microscopic image of an isolated blood vessel perfused for 10 minutes with a fluorescein-tagged cytotoxic fusion protein of the invention (i.e., Tat-P16 peptide). Fluorescence (bright streaks) is localized to the endothelial cells lining the blood vessel, demonstrating uptake of the peptide by these cells.

Tat-P16 peptides were prepared and labeled with fluorescein for use in uptake studies using intact blood vessels isolated from rat brain. Blood vessels were dissected from rat brain and stabilized in an isolated perfusion system in which vessels were attached on either end to catheters and placed under physiological pressure. Following a 10 minute perfusion of the isolated vessels with flurorescent Tat-P16 peptide (1 µM), vessels were examined for uptake of the peptides. Referring to FIG. 5, it is seen that the peptides were taken up by the endothelial cells of the vessels. No evidence was seen of uptake by the smooth muscle cells of the vessels. Within the endothelial cells, the labeled peptides were seen to be localized to the cell nuclei, further confirming uptake of the peptides by the cells.

Example 9

Production of Fusion Proteins in Transfected Cancer Cells In Vitro

To further determine if the fusion proteins were effective in killing cancer cells, studies were performed to test the effect of transfecting tumor cells in culture with plasmid vectors expressing the cytotoxic fusion proteins of the invention.

Constructs. Expression plasmids were constructed containing inserts encoding human or rat p16, p27 or a fusion of p27-p16, with and without a MPS and an alkaline phosphatase (AP) signal sequence. To facilitate construction and testing of various combinations of components, gene construction was of a modular design, such that different CCIs, MPSs and signal sequences could be easily interchanged. FIG. 4 is a schematic diagram showing the various elements of an expression plasmid of the invention, including the promoter sequence, and sequences encoding the fusion protein, which includes a signal sequence, a MPS and a CCI. Inserts were ligated into an expression plasmid previously described (Anwer K et al., Cancer Gene Ther 7:1156-1164, 2000). In some cases, inserts were cloned into an inducible expression system, such as the GeneSwitch expression system (Invitrogen, Carlsbad, Calif.).

Preparation of Lipid/DNA Complexes for Cell Transfection. Plasmid DNA was mixed with cationic lipids (DC-Chol/DOPE or DOTAP/DOPE) in 40% ethanol/5% dextrose. Ethanol and water were removed by lyophilization. The lipid/DNA lyophilized cake was hydrated with water and extruded through a 0.1 μm polycarbonate filter. Final DNA concentration was 0.2 mg/ml. Particle size was monodisperse with diameters <100 nm. Advantages of such small diameter particles included: (1) minimized RES clearance; (2) better access to tissue endothelium (3) reduced toxicity of complexes (4) complex storage capability at 4° C. in suspension for a minimum of 30 days, and (5) ability of transfection complexes to transfect cells in the presence of serum. By contrast, transient transfection complexes were inactivated by serum proteins and exhibited an exponential decay of activity over a 24 hour period.

Constructs were transfected into RG2 rat glioma cells and characterized for secretion, membrane permeability, and arrest of cells in G1. Cells were cotransfected with a plasmid expressing green fluorescent protein (GFP), to label the transfected cells, and were stained with anti-p16 or anti-p27 monoclonal antibody (MAb) to assess diffusion of gene product into non-transfected cells.

Example 10

Design and In Vitro Testing of Promoters Selective for Proliferating Cells

As described above, the expression of certain genes involved in DNA replication and cell cycle control is repressed in quiescent cells and stimulated upon re-entry into the cell cycle. Promoters that are strongly repressed in resting cells and/or are stimulated greatly in dividing cells were tested for the ability to direct expression specifically in proliferating endothelial cells.

1. Materials and Methods.

Plasmid Construction. A fragment of the cyclin A promoter spanning the region −215 to +100 (Henglein et al., *Proc Natl Acad Sci* 91:5490-5494, 1994) was isolated from human genomic DNA (Promega) using PCR and published primer sequences. The fragment created by the primers, i.e., (5'-GCGTCGGGCCCTAAATCC-3' (SEQ ID NO:6)) and (5'-CCCAGCTCGAGACCACGC-3' (SEQ ID NO:7)), was ligated into plasmid vector pCR2.1 (Invitrogen), to create plasmid pCA1135. The cyclin A promoter was isolated from a SacI fragment from a cloning plasmid and ligated into a plasmid backbone containing either the luciferase (pLC1154) or chloramphenicol acetyl transferase (CAT) expression cassette plasmids.

A fragment of the cdc6 promoter spanning the region from −130 to +7 (Williams et al, *Proc Natl Acad Sci* 94:142-147, 1997; Yan et al., *Proc Natl Acad Sci* 95:3603-3608, 1998) was constructed from two sets of oligonucleotides. Two sets of oligonucleotides were designed with the addition of a 5' SacI- and 3' BsmBI-compatible overhangs. Once annealed and ligated, the Cdc6 promoter was inserted into a GENEMEDICINE plasmid backbone to drive the expression of luciferase (pLC1284) or chloamphenicol acetyl transferase (pCT1330) reporter genes.

The mouse endothelin enhancer from −364 to −320 (Bu and Quertermous, *J Biol Chem* 272:32613-22, 1997) was synthesized using oligonucleotides, and annealed to produce a double-stranded 50-bp DNA fragment with 5' BglII- and 3' BamHI-compatible overhangs:

gatctGTACTTCATACTTTTCATTCCAATGGGGTGACTTTGCTTCTGGAG
(SEQ ID NO: 9)

aCATGAAGTATGAAAAGTAAGGTTACCCCACTGAAACGAAGACCTCctag
(SEQ ID NO: 10)

The fragment was multimerized by ligation at high concentration and digested with BamHI and Bgl II to eliminate head-to-head and tail-to-tail ligation products. The species containing four tandem copies was gel purified and inserted into a BamHI site upstream of the cyclin A and cdc6 promoters.

Within the constructs, the cyclin A or cdc6 promoter element was fused to UT12, a modified 5' untranslated region from the CMV immediate early gene, and IVS8, a synthetic intron. The reporter gene was either luciferase or CAT, and the 3' untranslated region and poly A site were from the human growth hormone gene (Blezinger et al, Hum Gene Ther 10:723-731, 1999). FIGS. 4 and 6 are schematic diagrams showing the design of the vector constructs.

Cell Culture and In Vitro Transfection. An in vitro transfection assay was designed to create a non-dividing vs. proliferating cell environment that would most closely resemble that found in vivo. Bovine aortic endothelial cells (BAEC) and human umbilical vein endothelial cells (HUVEC) were obtained from Clontech and maintained in EBM2 media+EGM2 nutrients. NIH 3T3 cells were obtained from ATCC and maintained in DMEM+10% FBS, 1% Pen/Strep, and 1% Glutamine. The day before transfection, the cells were seeded at $5 \times 10^5$ cells/well in 6-well plates. The cells were transfected with 1.0 μg of luciferase reporter plasmid plus 0.5 μg of the CMV-driven β-galactosidase expression vector pBG0956 as an internal standard. The DNA was complexed at a 1:6 (mass:mass) ratio of DNA:LipofectAMINE (Gibco-BRL) and then used to transfect the cells following the manufacturer's instructions. The cells were co-transfected with a β-galactosidase construct as an internal standard.

After transfection, the cells were trypsinized and re-plated into two wells of a 12-well plate. One well received 10% of the cells, to retain cells in a proliferating state, and the other well received 90% of the cells, to obtain confluency. Media was replaced after 24 hours and cells were harvested at 48 hr in Reporter Lysis Buffer (Promega). The level of β-galactosidase activity was assayed using the Galacto-Light reporter gene assay (Tropix). Luciferase expression was measured with the Promega luciferase assay kit (CT# E1501).

2. Results: In Vitro Screening of Promoter Activity in Endothelial Cells.

The effects of transfection with plasmids prepared as described above were observed in two endothelial cell lines (BAEC and HUVEC), and in one non-endothelial cell line, i.e., NIH 3T3 immortalized mouse fibroblasts. All three cell lines were quiescent after achieving confluence. The activity of the regulated promoters was compared to that of the intact CMV enhancer/promoter, to determine the effect of endothelial- or proliferation-specific regulatory elements.

Figure 7:
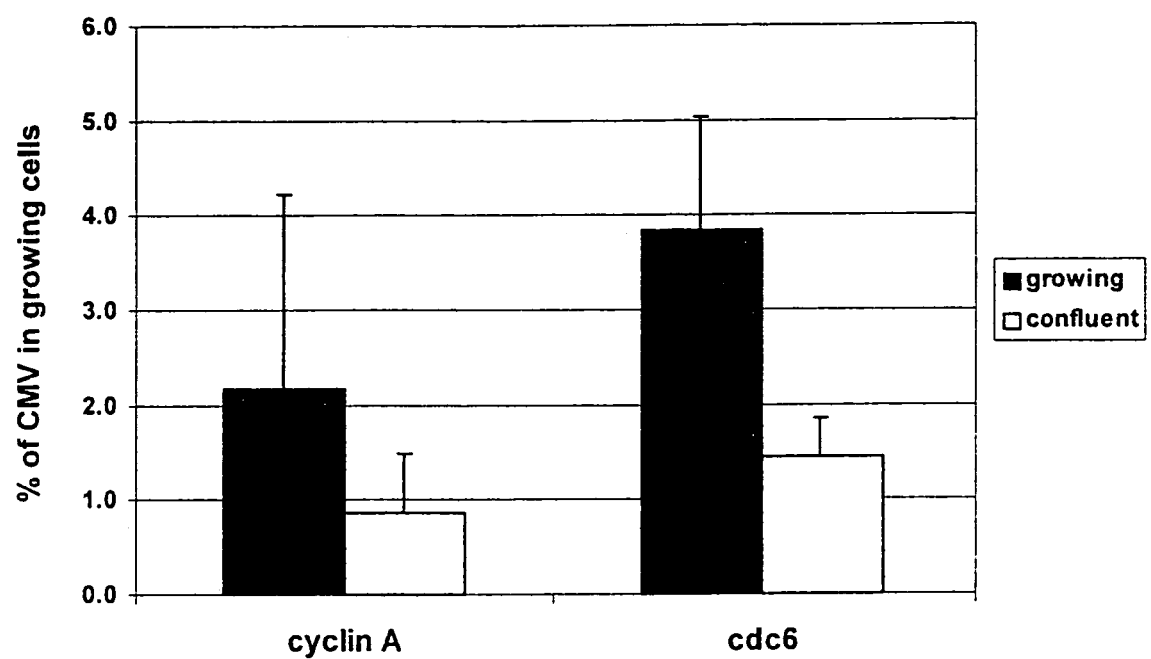
FIG. 7 is a graph showing transgene expression driven by cyclin A and cdc6 promoters in growing and quiescent NIH 3T3 cells.

Western blot analysis of total protein illustrated that the cells were not completely resting, however the validity of the technique was established at the level of reporter gene expression. Referring to FIG. 7, the results showed that the cyclin A promoter was about 2% as active as the CMV promoter in proliferating NIH 3T3 cells, and was repressed about 3-fold in confluent, contact-inhibited cells. The cdc6 promoter exhibited about 4% of the CMV activity in growing cells, and was also repressed about 3-fold in confluent cells.

Figure 8:
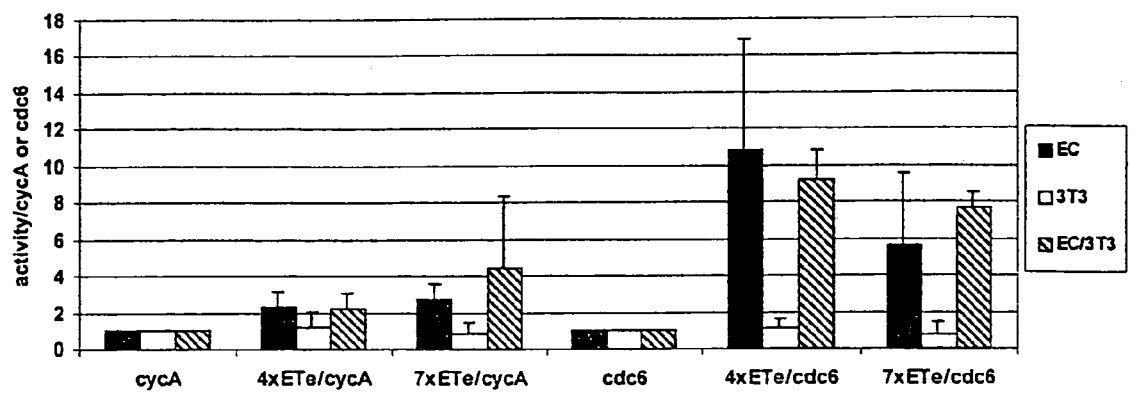
FIG. 8 is a graph showing the effect of incorporating an endothelin enhancer (ETe) domain into cyclin A and cdc6 promoter constructs. Activity of transgene expression was measured in cultured endothelial cells (EC) and fibroblasts (3T3).

As seen in FIG. 8, the addition of multiple copies of the endothelin (ET) enhancer to the cyclin A or cdc6 promoter provided for endothelial cell specificity, as well as proliferation specificity. The activity of the cyclin A promoter was increased several fold in endothelial cells relative to 3T3 cells, and the activity of the cdc6 promoter was increased over 10-fold in endothelial cells by the presence of four tandem copies of the ET enhancer (FIG. 8, 4×ETe/cdc6). The activity with seven copies of the ET enhancer linked to the cdc6 promoter was somewhat lower than with four copies (FIG. 8).

Figure 9:
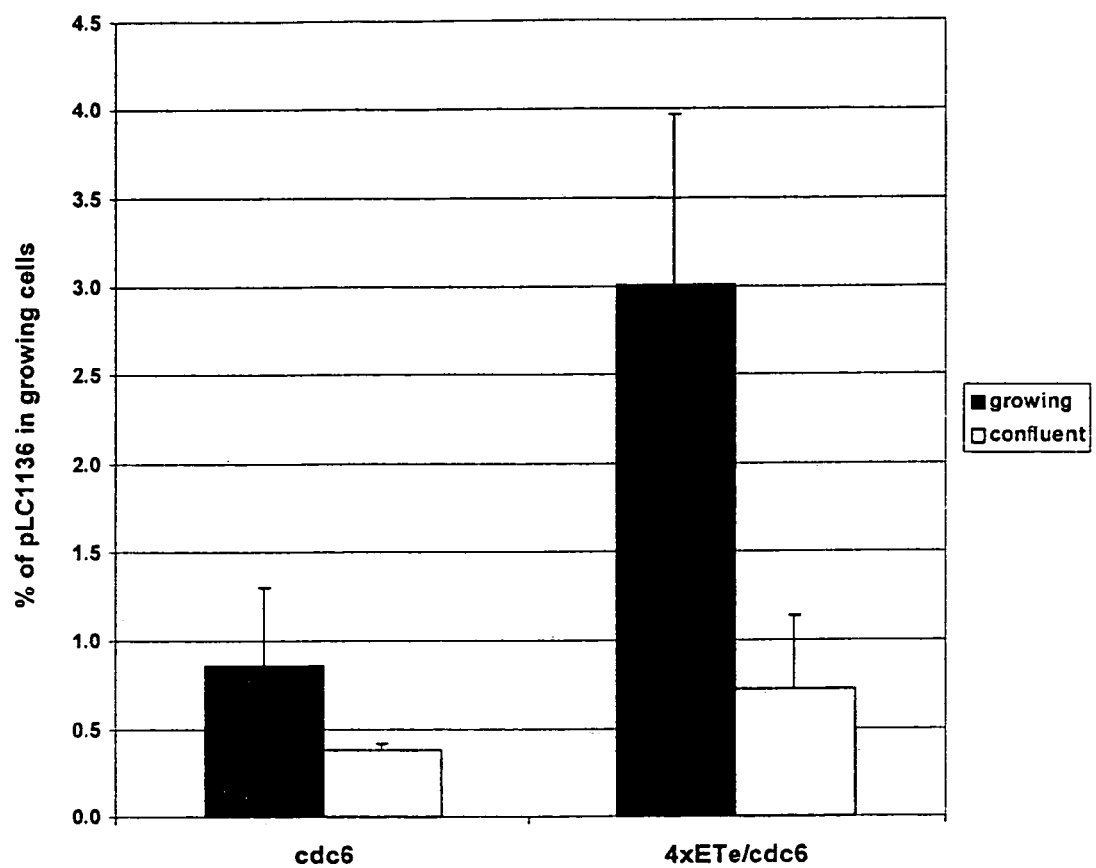
FIG. 9 is a graph showing activity of cdc6 promoter with and without ET enhancer in growing and confluent bovine aortic endothelial cells.

The 4×ET enhancer/cdc6 promoter construct was then tested in growing and confluent endothelial (BAEC) cells. As shown in FIG. 9, the activity in growing cells was about 5-fold higher than in confluent cells. This result demonstrated that the proliferation-specificity of the promoter was retained in the presence of the ET enhancer.

Example 11

Activity of Proliferating Endothelium Promoters In Vivo

Results from the above-described in vitro assays demonstrated that the highest level of overall expression, as well as endothelial- and proliferative cell-specificity was achieved with the 4×ETenhancer/cdc6 promoter construct. Accordingly, this vector was selected for testing of its efficacy in vivo in animal models of angiogenesis.

1. Materials and Methods

In Vivo Transfection. Plasmid DNA, prepared as described above, was fermented, isolated and purified from *Escherichia coli*, with <50 endotoxin units (EU)/mg. DOTMA (1,2-Di-O-Octadecenyl-3-Trimethylammonium Propane) and cholesterol were purchased from Avanti Polar Lipids, Inc. (Alabaster, Ala.). DOTMA:CHOL (4:1 m/m) SUV liposomes were prepared by hydration of the lipid film and probe-sonication, followed by centrifugation and sterile filtration. DNA-lipid complexes were formed by mixing plasmid DNA with liposomes at ⅓ (−/+) charge equivalent in 10% lactose. The particle size was 127 nm±14 nm (mean±std, n=8), measured by a laser light scattering system (Model B1-9000, Brookhaven Instruments Corporation, Holtsville, N.Y.). The zeta potential was 45 mV±8 (mean±std, n=3), measured by Zetasizer Model DTS5200 (Malvern Instruments, Southborough, Mass.). Gel electrophoresis showed complete condensation of the complexes.

Animal Models. A mouse model of tumor formation was used to test the efficacy of the fusion proteins. Subcutaneous solid tumors were created in 6-8 week old female C3H mice (20-22 g) by subcutaneous injection of $4 \times 10^5$ squamous carcinoma cells (O'Malley et al., 1997). A second mouse model was used in which endothelial cells are stimulated to divide. Ovariectomized C3H mice (Charles River Laboratories) were treated with 50 μg estradiol benzoate (Sigma Chemical Co., St. Louis, Mo.) by subcutaneous injection once a day for four days before plasmid injection (90 μg in 300 μl). Under these conditions, the endothelial cells of the uterine vasculature are stimulated to divide, proliferate, and form new blood vessels.

Transfection complexes carrying a CAT expression plasmid were administered intravenously by tail vein injection into tumor-bearing or ovariectomized mice. Mice injected with 10% lactose were used as controls. Tissues (tumors, uterine and lung samples) were harvested after 18 h or 4 days unless indicated otherwise, and analyzed for CAT expression.

Assay for CAT Expression in Mouse Tissues. Tissue extracts were prepared by homogenization of tissue in five volumes of TENT buffer (Tris 10 mM, EDTA 1 mM, NaCl 0.1 M, Triton X-100 0.5%). Tissue homogenates were centrifuged at 10,000×g for 15 min and supernatant was assayed for CAT using an enzyme-linked immunofluorescent assay (ELISA) (Boehringer Mannheim, Indianapolis, Ind.).

2. Results

Ovariectomized Mouse Model. A construct carrying the 4×ETe/cdc6 regulatory element driving the CAT gene was complexed into liposomes and injected into the tail vein of ovariectomized mice. Previous experiments have demonstrated that most systemically administered DNA is taken up by the lung vasculature. The lung tissue, in which the endothelial cells are not dividing, therefore provided a good control for the proliferation-specificity of the construct.

Figure 10:
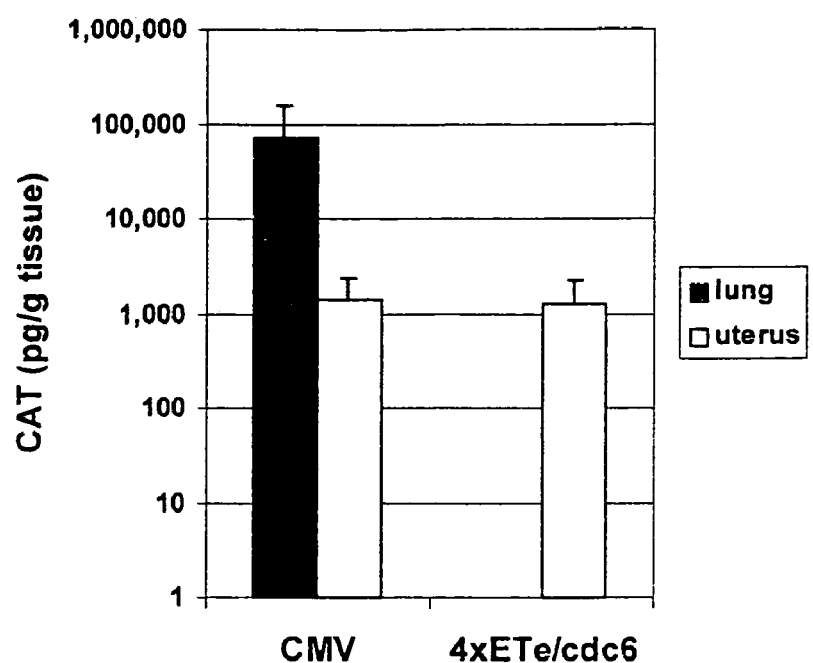
FIG. 10 is a graph showing activity of a hybrid proliferating cell/endothelial cell promoter of the invention (i.e., 4×ET enhancer/cdc6 promoter) in an ovariectomized mouse model of angiogenesis. In this model, angiogenesis (characterized by proliferating endothelium) is stimulated in the uterus but not in other tissues, such as lung. Under control of the 4×ETe/cdc6 promoter, expression of the CAT transgene is seen only in the uterus. A CMV promoter, by contrast, drives CAT expression constitutively in both uterus and lung tissues of these animals.

Results showed that the activity of the promiscuous CMV promoter was nearly 100 times higher in the lung than in the uterus, whereas the activity of the 4×ETe/cdc6 construct was as high as CMV in the uterus, but completely repressed in the lung (FIG. 10). In mice that were not treated with estradiol, the activity of the 4×ETe/cdc6 construct was nearly undetectable in both lung and uterus. This result indicated that the 4×ETe/cdc6 regulatory element can provide the specificity needed to localize expression of a therapeutic gene to the angiogenic vasculature.

Figure 11:
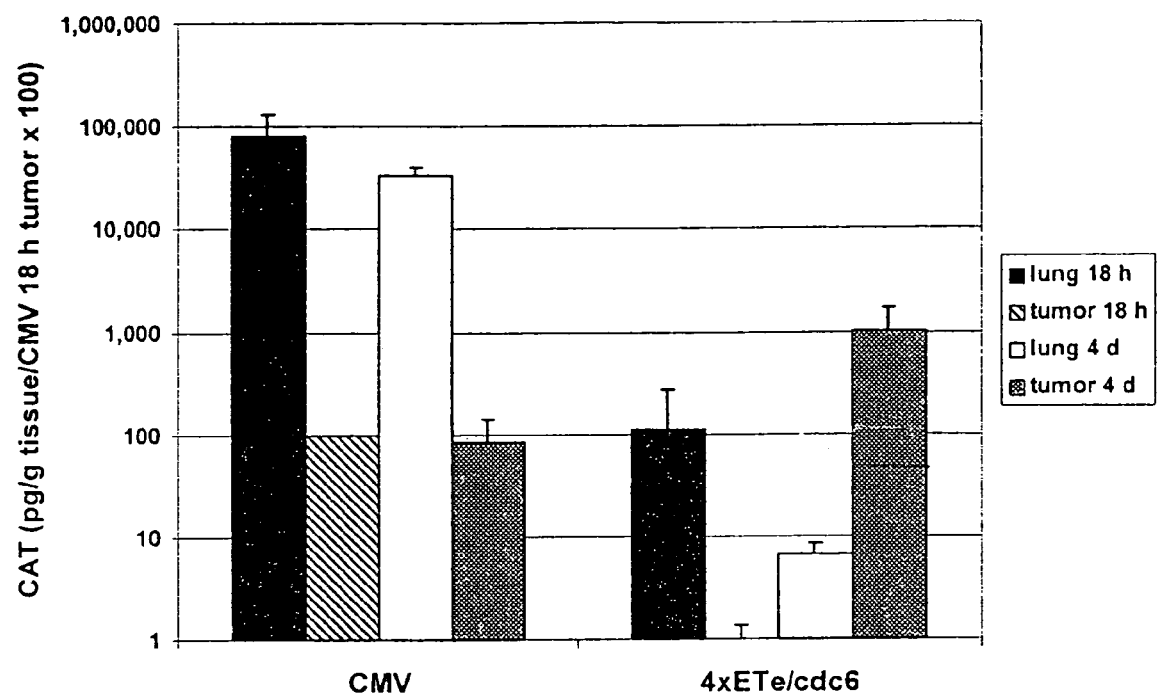
FIG. 11 shows activity of 4×ET enhancer/cdc6 promoter in a mouse tumor model at 18 h and 4 d after plasmid injection. Fours days after administration of plasmid complexes, expression of the transgene is 10-fold greater in tumors transfected with vectors containing the proliferating cell/endothelial cell-specific promoter.

Mouse Tumor Model. Specificity for proliferating endothelial cells was confirmed using a second model of angiogenesis; i.e., mice implanted with SCCVII tumor cells. In this model, angiogenesis is occurring in the tumor, but not in the lung. After the development of a subcutaneous tumor, mice were injected intravenously with liposome/plasmid complexes, and tumor and lung tissues were assayed for CAT expression at 18 h and 4 d. As in the study using ovariectomized mice, most of the DNA was taken up by the lung endothelium. Referring to FIG. 11, results showed that with the CMV promoter, CAT activity was nearly 1000-fold higher in the lung than in the tumor at 18 h. At 4 d, CMV activity decreased significantly in the lung, but not in the tumor. By contrast, the 4×ETe/cdc6 promoter behaved quite differently. At 18 h, its activity in the lung was 1000-fold lower than that of CMV, and was undetectable in the tumor. At 4 d however, its activity in the tumor increased to more than 10 times that of the CMV promoter (FIG. 11). This finding demonstrated that the construct was repressed in the non-dividing endothelial cells of the lung, but was very active in the dividing endothelial cells of the tumor vasculature. Therefore this promoter is suitable for specifically driving transgene expression in proliferating endothelial cells in vivo.

Figure 12:
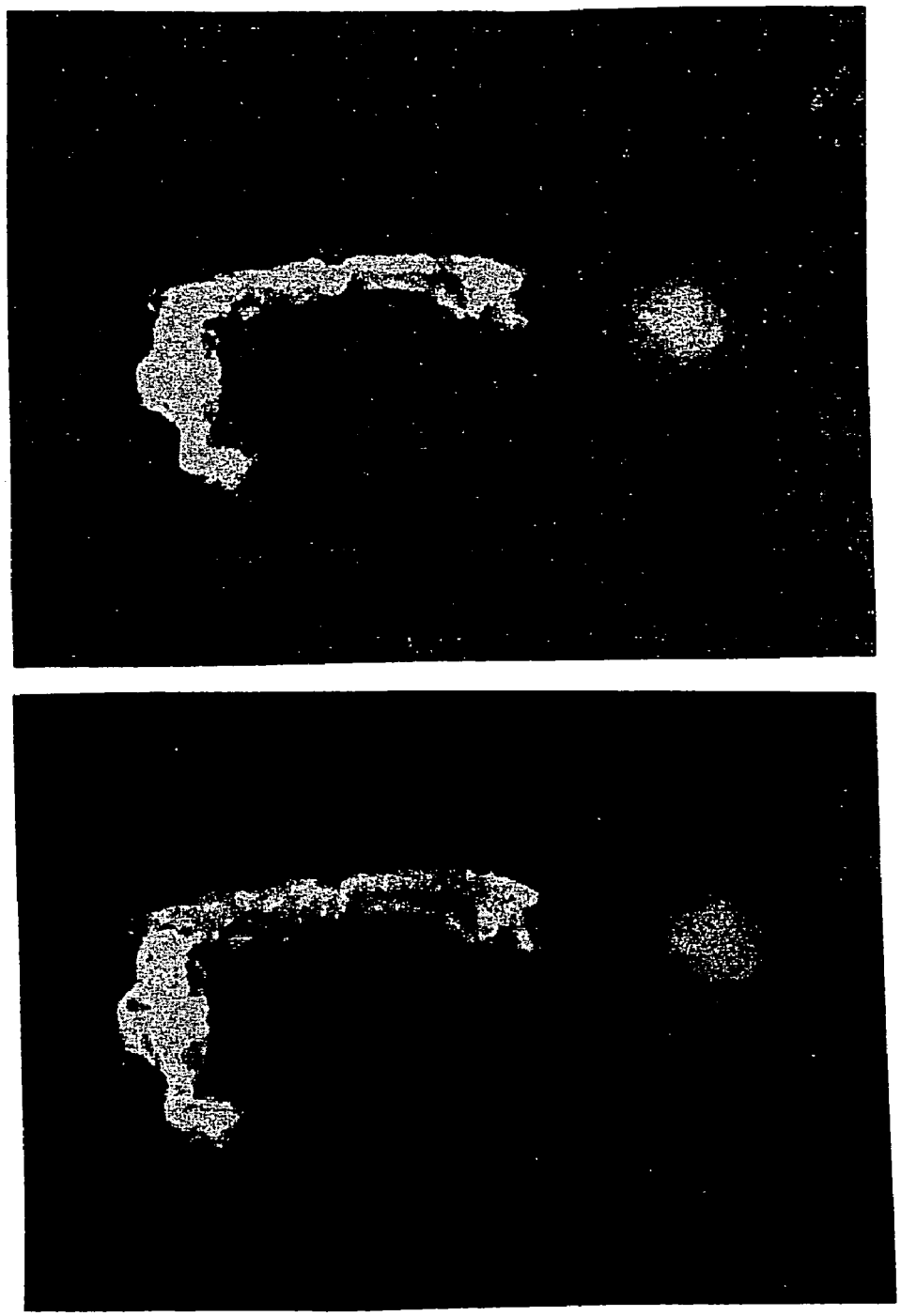
FIG. 12 is two micrographs of rat brain showing fluorescence (upper and lower panels) and phase contrast (upper panel) images of rat brain following systemic injection of lipid/DNA complexes of the invention. A blood vessel within a tumor is brightly fluorescent, indicating expression of the transgene (GFP) driven by a proliferating endothelial-cell specific promoter.

In other studies using rats, lipid/DNA transfection complexes containing a GFP expression plasmid were directed to the brain by intra-arterial (IA) administration through the carotid artery. FIG. 12 is a pair of phase and fluorescent micrographs showing expression of GFP in a blood vessel of a tumor in the RG2 rat brain following injection. This result indicated that the fusion proteins of the invention could also be delivered systemically as lipid/plasmid complexes to blood vessels in the brain. The plasmids subsequently entered the endothelial cells of the blood vessels, as evidenced by expression of the fluorescent transgene in these cells.

Example 12

Orientation of Tat Affects Efficiency of Killing

Cell killing by a fusion protein containing Tat at the C-terminus of p14 and at the N-terminus of p14 was examined. Placing Tat at the C-terminus of p14 resulted in a higher level of cell killing than was achieved by a fusion protein containing Tat at the N-terminus.

Example 13

Therapeutic Gene Development

To be an effective cancer therapy, a majority of the tumor cells must be impacted by the gene transfer, either directly or indirectly. Current gene delivery systems, both viral and non-viral are incapable of achieving this goal. For this reason, gene expression must produce a bystander effect such that all the cells in contact with the transfected cells are killed or permanently growth arrested. To achieve this the cytotoxic gene product is engineered to be secreted from the transfected cell using a secretory signal sequence and include a membrane permeability domain at the N- or C-terminus that can shuttle the cytotoxic domain into non-transfected cells and back into transfected cells.

Additional Membrane Permeability Domains

Synthetic peptides labeled with an N-terminal fluorescein were synthesized to test the ability of a shuttle domain to enter brain tumor and endothelial cells. The amino acid sequences for the shuttle domain was derived from HIV Tat amino acid 47 to 56 (YGRKKRRQRR SEQ ID NO:23) (Robert-Guroff et al., *J. Virol.* 64:3391-3398, 1990) to which AGGG was added to the N-terminus, and the antennapedia homeodomain from *drosophila* (ANT) (RQIKIWFQNR-RMKWKK SEQ ID NO:24) (Astriab-Fisher et al., *Pharm. Res.*, 19:744-754, 2002). A synthetic peptide (PTD-5) reported to have similar properties as Tat and ANT was also tested (Mai J. C. et al, *Cancer Res.* 2001; 61: 7709-7712.). Uptake was tested in two human glioblastoma cell lines and a rat glioma cell line, the latter being used for the rat brain tumor model. A 1 µM concentration of each peptide was added to $10^6$ cells in a 6 well plate. Fluorescence microscopy showed that the Tat peptide preferentially labeled the cell nuclei whereas the ANT peptide stained the cytoplasm for all three cell types whereas the PTD-5 showed no fluorescence labeling of either of the three cell types. The Tat and ANT peptides were doubled in length by the addition of MVR-RFLVTLRIRRA (SEQ ID NO: 25), amino acids 42 to 55 from a human cyclin-dependent kinase inhibitor 2A (melanoma, p16, inhibits CDK4) (CDKI), transcript variant 4, mRNA (accession no. NM_058195). This domain binds MDM2 and inhibit ubiquination of P53, a tumor suppressor protein. The addition of this second domain did not affect the ability of Tat and ANT to enter cells but it did result in cell killing. The results from cell killing experiments are shown in Table 3. Only the combination of Tat-CDKI was toxic to the cells, 65% killing for T98G and 61% killing for RG2 cells. The Tat and CDKI showed no toxicity in T98G and CDKI showed some toxicity, 22%, in RG2 cells. Similar results were obtained with A172 cells. Substitution of the ANT amino acid sequence for the Tat sequence yielded similar results. However, cell killing was about 10 to 15% less for all three cell types.

TABLE 3

Fusion Peptide Mediated Cell Killing of Human Glioblastoma (T98G) and Rat Glioma (RG2) Cells.

| Peptide | T98G Cells % Viable Cells | StDev | RG2 Cells % Viable Cells | St.Dev. |
|---|---|---|---|---|
| Tat-CDKI | 35.2 | 3.5 | 39.0 | 1.6 |
| Tat | 95.0 | 0.9 | 94.0 | 1.6 |
| CDKI | 94.4 | 1.9 | 77.7 | 3.9 |

Cells were plated in 6 well plates and 10 µM of each peptide was added in complete media and incubated for 1 hr. Cells were removed from plate using a commercially available cell stripper, resuspended in Ringers, stained with propidium iodide and analyzed by FACS to determine the number of viable cells. n = 3

Example 14

Dose Response of Fusion Peptide Cell Killing of RG2 Cells

Figure 13:
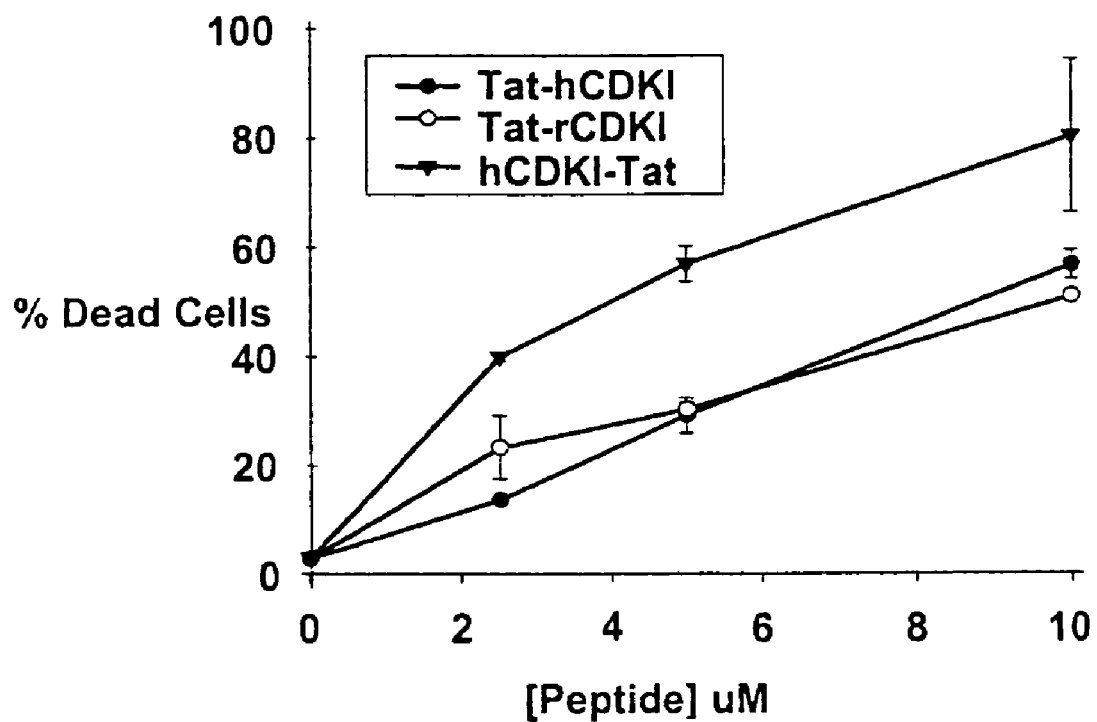
FIG. 13 is a graph of a dose response of fusion peptide cell killing of RG2 cells. hExon1 is human exon 1 and rExon1 is rat exon 1. Tat is at the C-terminus for hExon1-Tat.

There are 4 conserved amino acid differences between the rat and human CDKI sequence. Both sequences were attached to Tat and tested for cell killing activity in the rat glioma RG2 cells. Also the effect of orientation of the Tat and CDKI domains were tested. RG2 cells were plated on 6 well plates at approximately 70% confluency. Each of the peptides was added to the wells with increasing concentration. After 1 hr, cells were removed from the plates, washed 2× with PBS, stained with propidium iodide and analyzed by FACS for viable cells. A dose response curve is shown below in FIG. 13 where all three peptides were tested. The results obtained with the rat and human CDKI sequences are superimposable, showing that the change in amino acid sequence did not affect cell killing. Secondly, exchanging the CDKI domain for the Tat domain increased cell killing from 65% to 80% cell killing at 10 µM.

The peptides are fairly labile in the media and approximately 50% are degraded upon incubation at 37° C. in complete media (qualitative analysis by PAGE) after 1 hour. Hence, incubation times were not tested for more than 1 hour. Uptake of these peptides and cell killing activity was tested in a 3 dimensional organ culture using rat cerebral arteries cultured under physiological pressure and flow. A segment of the rat cerebral artery is surgically removed and placed in ringer's solution. Using a surgical stereoscope, the blood vessel is tied at either end to two cannulas on a teflon stage. Ringer's solution is perfused through the lumen of the vessel at a constant rate that maintains physiologic hydrostatic pressure. The fluorescent peptide was introduced intraluminally by perfusing a 1 µM solution of peptide through the lumen over a 10 minute period.

Example 15

Figure 14:
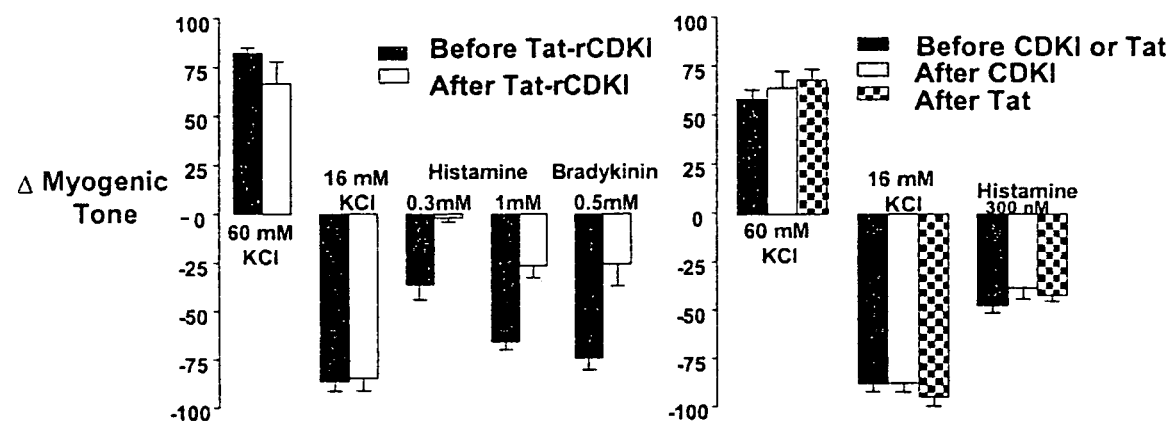
FIG. 14 is a pair of graphs showing an effect of Tat-rExon1 on endothelial cell and smooth muscle cell vasodilation and construction.

Effect of Tat-rExon1 on Endothelial Cell and Smooth Muscle Cell Vasodilation and Construction Similar observations as those described in Example 2 for the Tat peptide were made for fluorescein-ANT peptide and fluorescein Tat-cCDKI with regard to restriction of labeling to the endothelial cells. However, 30 minutes after exposing the blood vessels intraluminally to the Tat-rCDKI, the morphology of the endothelial cells was altered. The biological response of both the endothelial cells and the smooth muscle cells was tested before and after addition of the Tat-rCDKI peptide. The results are shown in FIG. 14.

The blood vessels were put in culture described above and perfused with buffer of the same composition as cerebrospinal fluid. Vessel diameter was measured before and after administration of each reagent. 3 µM of each peptide was perfused through for 10 minutes followed by a 10 minute wash through. Vasoconstriction and vasodilation were determined for each vessel before peptide was applied. Perfusion was continued until the vessels relaxed to their original diamter (approximately 30 minutes). The vasoconstriction and vasodilation reponse was remeasured after the 10 minute wash through. The 60 mM KCl and 16 mM KCl conditions are smooth muscle vasodilator and constrictor, respectively. Histamine and Bradykinin are endothelial cell vasodilators. The panel on the left hand side of FIG. 14 shows the effects of Tat-rCDKI peptide on the response of the organ culture to each of these reagents. The panel on the left side are the controls and shows the effect of Exon1 peptide or Tat peptide on the response of the organ culture to each of these reagents. The Tat-rExon1 peptide showed the inhibition of vasodilation whereas the smooth muscle cells showed no effect, consistent with the above observation that the peptide is only able to penetrate the endothelial cells and not affect the smooth muscle cells.

Propidium iodide staining of the blood vessels showed only the endothelial cells were affected by the Tat-rExon1 peptide whereas no PI stained nuclei were observed for the Exon1 or Tat treated vessels. No PI statined smooth muscle cell nuclei were observed. Collectively, these results show that a Tat or ANT amino acid sequence can penetrate both human and rat glioma cells. Secondly, addition of a cell killing domain to either peptide resulted in cell killing whereas the membrane permeability peptide or cell killing peptide alone showed no activity, thus validating this sequence. The organ culture studies show that blood vessel smooth muscle cells and endothelial cells are able to take up the Tat, ANT, Tat-CDKI and ANT-CDKI peptides. Secondly, uptake of the Tat-CDKI peptides by the endothelial cells resulted in lack of response to vasodilators and upon further analysis showed that these cells were dead whereas, the adjacent smooth muscle cells were not affected. Hence, both tumor cells and endothelial cells were responsive to the cell killing activity of the Tat-CDKI.

Without wishing to be bound by theory, a gene encoding for a fusion peptide composed of a membrane permeability domain combined with a cell killing domain can be transfected into cells and the resulting gene product is secreted, enters the non-transfected cells and kills them.

An expression plasmid containing the $CMV_{enhancer}$/Chick β-$Actin_{promoter}$ is constructed that encodes for the fusion peptide. The genes encode for the following amino acid sequences:

| General Secreted Membrane Permeability-CDKI Gene Diagram | | | | |
|---|---|---|---|---|
| Hind III | BamH I | Nsi I | Xba I | Nco I |
| Secretory Signal Sequence | Membrane Permeability Sequence | Cytotoxic Sequence | Extrinsic Epitope Tag | Poly-A-Signal |

The design of the gene is modular with unique restriction sites flanking the 5' and 3' end of each segment. This enables new sequences to be readily exchanged for testing and very little if any extra sequence is introduced. The sequences that are tested to show that the expressed protein can be secreted from transfected cells and penetrate adjacent cells are listed in the table 4 shown below. Expression of the protein gene product are followed using an extrinsic epitope tag, i.e., influenza hemaglutinin (HA).

TABLE 4

List of Membrane Permeability Domains and CDKI Domains

| | Membrane Permeability Domain | Species | P14ARF exon 1-β |
|---|---|---|---|
| HIV-Tat | AGGGYGRKKKRRQRRR (SEQ ID NO: 26) | Human | MVRRFLVTLRIRRA (SEQ ID NO: 25) |
| Antennapedia Homeodomain (ANT) | RQIKIWFQNRRMKWKKKGG (SEQ ID NO: 27) | Rat | MGRRFVVTVRIRRT* ( SEQ ID NO: 28) |

*Accession No. AF474975

Alkaline phosphatase signal sequence was selected based on the observation that multiple cell types can secrete human placental alkaline phosphatase, such as skeletal muscle, hepatocytes and endothelial cells. The Tat and ANT sequences are compared for degree of penetration into adjacent cells and the subsequent degree of cytotoxicity. Cell types tested are A172 and T98G cells, both human glioblastoma cell lines; RG2 cells, a rat glioma cell line; and human brain microvascular endothelial cells (HBMECs). Western blots are used to verify that each cell type can synthesize and secrete the dual domain protein. Immunohistochemical staining is used to verify that the dual domain protein can enter untransfected cells adjacent to the transfected cells. Cell killing experiments are used to verify the biological activity of dual domain protein.

Example 16

Cationic Lipoplexes

A method for formulation of cationic lipids has been devised that yields stable complexes when stored at 4° C. as a suspension. The cationic lipids are suspended in 40% ethanol, 5% dextrose and added to plasmid DNA. The mole ratio of cationic lipid to DNA nucleotide is 3:1 for DC-Chol, DOTAP and Genzyme Lipid 89 (a dioleoylspennine carbamate). The ethanol is removed by evaporation and the cationic lipid/DNA powder is resuspended in $H_2O$ with a final plasmid DNA concentration of 0.2 mg/ml. The resultant suspension is composed of particles with an average diameter between 70 nm to 150 nm depending upon the cationic lipid and helper lipid. They can be stored as a suspension at 4° C. for up to 1 month and stored as a lyophilized powder for at least 6 months. Another important feature of the transfection complexes is their ability to transfect cells in the presence of serum.

Example 17

Figure 15:
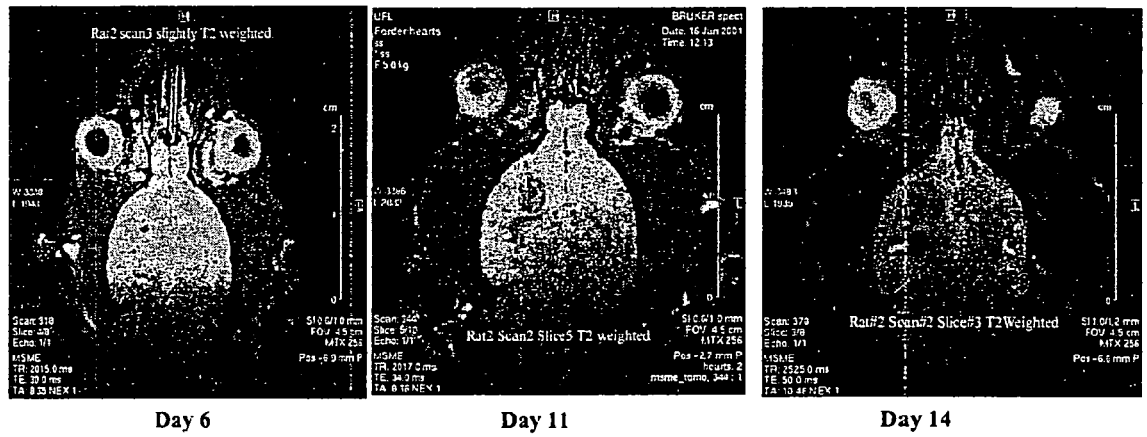
FIG. 15 is a series of sequential T2 weighted MRI images of rats after implantation of RG2 cells into the striatum. The tumor is the circular object in the left hand side of each image.

Implantation of RG2 Cells Into the Striatum and Histochemical Staining of Rat Brain Tumors The ethanol transfection complexes were tested for in vivo gene transfer using a syngeneic rat brain tumor model. RG2 cells were implanted into the striatum of 225 gram male fisher rats in a volume of 2 µl. The cells were injected at a rate of 1 ul per minute with a 2 min adsorption time before the needle is withdrawn. The tumor growth rates were measured by calculating the tumor volume from MRI images. Life expectancy from time of tumor implant is 21 days. The tumors are refractory to chemotherapy and radiation. FIG. 15 shows the increase in tumor size as a function of time.

$1 \times 10^5$ RG2 cells were stereotactically implanted into the striatum of male Fischer rats on day 0. Coronal images of tumors were obtained using a 4 Tesla MRI on days 6, 11 and 14. These MRI images were from the same rat. Five to 7 days after tumor implantation, the tumors were 0.5 to 1 mm in diameter. Between days 10 to 12, the average diameter was 2 mm and by day 14 to 16, the diameters increased to 4 to 6 mms.

Figure 16:
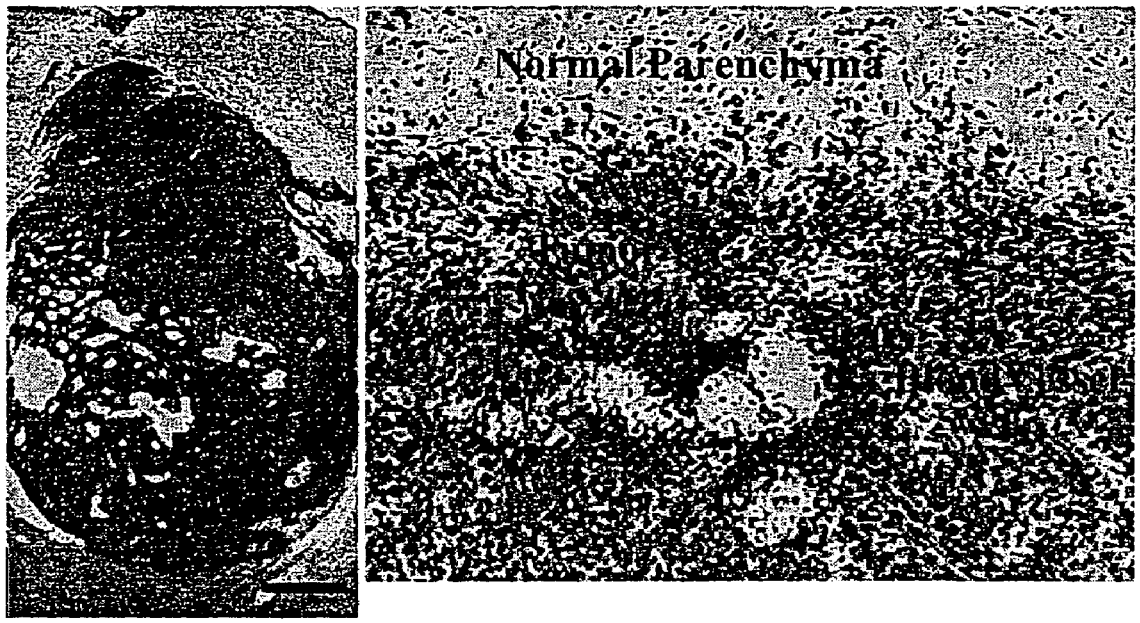
FIG. 16 is a pair of micrographs showing histochemical staining of rat brain tumors on day 16 after RG2 cell implantations. The micrograph on the left is at 30× magnification. The bar is 1 mm. The micrograph on the right is a 100× magnification.

Rats were euthanized on day 16 after tumor implantation and perfused with fixative. Brains were cut in 40 µm sections with a cryostat and stained with hematoxolin and eosin (H&E stain). Histochemical analysis showed that once the tumors reach 2 mm, the centers begin to necrose. The tumors also become highly vascularized. By days 14 to 16 there is a high degree of necrosis in the center of the tumor. A typical histochemical section through the center of the tumor is shown in FIG. 16. As shown in the left panel, the late stage tumor begins to close off the ventricles and infiltrate into the cerebral cortex. It also shows the high degree of necrosis in the center of the tumor. The higher magnification in the right panel shows infiltration of the tumor cells into the normal parenchyma and also shows a few of the numerous blood vessels in the tumor.

Example 18

Tail Vein Administration of Fluorescent Labeled Transfection Complexes

Rats were implanted with $5 \times 10^4$ RG2 cells in 2 µls at a rate of 1 µl/min into the rat striatum. 8 days after tumor implantation, 0.45 mg plasmid DNA dose was administered via tail vein in a volume of 1 ml 5% dextrose. Tissues were harvested 2 hours after injection and processed for fluorescent light microscopy. Cell nuclei were labeled with DAPI and the transfection complexes were labeled with red (lipid) and green (DNA) fluorophores. Localization of ethanol transfection complexes was visualized by labeling the plasmid DNA with a fluorescein-psoralen conjugate that was UV crosslinked to the plasmid DNA. The lipid component of the transfection complex was labeled with rhodamine-DOPE at 0.5 mol %. Localization of the fluorescent-labeled ethanol transfection complexes in tumor bearing rats following systemic administration was examined There was far more lipid than DNA and hence, the red fluorescence predominates at the lower magnification but flecks of green were interspersed within the red fluorescence at the higher magnifications. The low magnification showed red streaks throughout the tumor whereas no red fluorescence was observed in the image from the non-lesioned contralateral side. The streaking staining patterns resembled that of endothelium.

Example 19

CAT Expression in Rat Brain Tumor and Lung Following Tail Vein Administration of Stable Transfection Complexes Quantitative PCR (qPCR) analysis of a CAT plasmid packaged in the transfection complexes yielded 0.5% of injected dose in the brain with 3-fold higher accumulation in the tumor bearing lobe compared to the non-tumor lobe. Expression studies using several different probes, including expression of green fluorescent protein, and immunohistochemical staining of CAT could not detect any fluorescent cells. Analysis of brain and lung RNA 12 hours after administration of transfection complexes showed expression for two different genes, CAT and endostatin. Rats injected with transfection complex were analyzed and RNA was obtained from a rat injected with 10% lactose. A 242 base pair band was observed and represents a portion of the CAT RNA that includes part of the 5'UTR and part of the coding region. A slower migrating band was observed represents plasmid DNA that was localized in the tissue but not completely digested by the DNase. The expression cassette contains an intron between the 5'UTR and the initiation codon. The primers are complementary to the 5'UTR and the coding sequence for CAT. Hence, the RNA band is smaller than the DNA band due to RNA processing. The results show that there is CAT RNA in the tumor bearing lobe and the lungs but not in the contralateral lobe.

In an effort to minimize delivery of transfection complexes to other organs and to decrease the effective plasmid DNA dose, transfection complexes were administered into the carotid artery through a catheter. The transfection complexes were prepared with a plasmid encoding a green fluorescent protein (GFP) gene driven by a $CMV_{(enhancer)}$/Chick $\beta$-$Actin_{(promoter)}$. This is a very strong promoter compared to CMV promoter controlling CAT expression. Fifty and 100 µg plasmid doses were tested but only the 200 µg dose showed GFP expression.

Expressing the therapeutic gene under the control of a promoter that is active in proliferating endothelium is the third safeguard in achieving selective expression of a therapeutic gene in the tumor vasculature. Many different promoters using in vitro transfection of endothelial and non-endothelial cells in a proliferative and non-proliferative mode, were screened. Promoters that should be responsive to endothelial proliferation signals did not yield strong expression compared to a non-selective CMV promoter. This focused efforts to promoters active in the cell cycle. These proved to be selective but were also very weak compared to the CMV promoter. Addition of the CMV enhancer, increased promoter strength but reduced selective expression. The endothelin enhancer (Bu X, Quertermous T. *J Biol Chem* 1997; 272: 32613-32622.), increased promoter strength. The cdc6 promoter (cdc6p) was found to work best with either a 4× or 7× multimerized endothelin enhancer (ETe) in transfection of HUVECs and BACs.

A murine 4×ETe/cdc6p was incorporated into an expression cassette containing a CAT reporter gene with a CMV exon/intron and a human growth hormone poly adenylation signal. The UT12 and IVS8 are consensus intron/exon splice sequences for mRNA processing. The plasmid was formulated into a stabilized transfection complex and administered to ovarectomized mice that had been injected with estradiol for 4 days prior to administration of the transfection complexes. The estradiol induced the hypervascularization of the uterus creating a highly active environment of proliferating endothelium due to induction of angiogenesis. Control complexes consisted of an expression plasmid with the CMV enhancer/CMV promoter and the exact same expression cassette with regard to intron/exon, reporter gene coding sequence and poly A signal. The only difference was the promoter. This allowed the direct comparison of promoter strength and selective expression.

The activity of the 4×ETe/cdc6 promoter was equivalent to the CMV promoter plasmid in the uterus but was undetectable in the lungs. In mice that were not treated with estradiol, the activity of the 4×ETe/cdc6 construct was nearly undetectable in both lung and uterus. This result suggests that the 4×ETe/cdc6 promoter provides selective expression in proliferating endothelium and the promoter strength is equivalent to the CMV promoter.

The CAT expression levels obtained with this promoter vs. the CMV promoter was also tested in a mouse tumor model in which subcutaneous solid tumors were created in 6-8 week old female C3H mice (20-22 g) (Charles River Laboratories Raleigh, N.C.) by S.C. injection of 4×105 squamous carcinoma cells (SCCVII). Transfection complexes containing CAT expression plasmid under the 4×ET (e)/cdc6(p) or CMV(e)/CMV(p) were administered intravenously into tumor bearing mice at a 3 mg/kg plasmid dose. Mice injected with 10% lactose were used as controls. Tissues were harvested for CAT expression 18 h and 4 days after administration.

The CMV promoter yielded 100 ng of CAT/gm of tissue in the lung 18 hours after administration and 40 ng of CAT/gm of tissue 4 days after administration. For the ET/cdc6 promoter, 100 ng of CAT/gm of tissue was detected in the lungs 18 hours after administration and no CAT protein was detected 4 days later. In the tumor, the CMV promoter yielded 100 pg of CAT/gm of tissue in the tumor 18 hours and 4 days after administration. The endothelin enhancer/cdc6 promoter yielded barely detectable levels of CAT 18 hours after administration but on day 4 yielded 1 ng of CAT/gm of tissue. Hence, the endothelin enhancer/cdc6 promoter yielded 400 fold less expression than the CMV promoter in the lungs and ten fold higher expression in the tumor 4 days after administration.

Example 20

Fusion Peptide Expression

RG2 cells, A172 cells, T98G cells and HBME cells are transfected with the pTat-CDKI expression plasmid containing the Tat membrane permeability domain, the CDKI sequence and an HA tag. Cells are transfected with the following control plasmids:

TABLE 5

Components of Plasmids for Penetration into Non-Transfected Cells and Assayed for Cell Killing

| Plasmid Name | Secretory Signal | Tat sequence | CDKI | HA |
| --- | --- | --- | --- | --- |
| pVC1157 | − | − | − | − |
| P16-1000 | − | − | + | + |
| P16-1001 | − | + | + | + |
| pTat-CDKI | + | + | + | + |

Cell lysates and cell supernatants are analyzed for protein by western blot. The reason for assaying expression in all cell types is to ensure that all cell types are able to express the transgene. T98G and A172 cells are human glioblastoma. RG2 are the rat glioma used for the rat model and HBMECs are endothelial cells that are used for testing polarized secretion of the transgene in a transwell assay.

Plasmids used for western analysis, immunohistochemical identification of secretion and diffusion into non-transfected cells and cell killing are listed in Table 5. The A172, T98G and RG2 cells have been tested for expression of the Tat-CDKI-HA gene product. Western blots show a band in the proximity of the 3.5 kDa marker. The calculated MW of the gene product without the signal sequence is 3.1 kDa. The above constructs are used to test cell entry. This is done in two ways. The first is to transfect a single cell type in triplicates with 0.5, 1.5 and 5 µg of DNA with p16-1000, p16-1001 plasmid and pTat-CDKI. The percentage of transfected cells are determined by immunohistochemical staining of cells that are first fixed and then permeabilized prior to antibody staining. Quantitation of transfected cells is done by FACS after the cells have been removed from the plate or by morphometric microscopy.

Once it has been established that the protein enter adjacent cells, a cell killing assay is conducted as a function of the plasmid dose response using the same plasmids, pTat-CK|DKI, p16-1000, p161001 and p16-1002. Cell death is measured by counting cell numbers 48 hours after transfection. Cells are plated at a lower confluency to allow for at least two doublings before cell numbers are measured.

The peptide studies have shown that both ANT and Tat peptides can enter cells and that addition of another 14 amino acids does not affect cell entry. Expression and secretion of the peptide should yield entry of the protein into adjacent cells. Western blots from transfected cell pellets have shown that the peptide can be translated and supernatants are analyzed. The protease furin has been shown to be active intracellularly and extracellularly in astrocytomas. A mammalian expression vector for synthesis of angiotensin peptides fused the sequence to the heavy chain of IgG with a RVRTKR (SEQ ID NO: 29) sequence separating the angiotensin peptide from the IgG. Upon secretion, the endogenous furin cleaves the fusion gene product releasing the angiotensin peptide. This same strategy can be applied to the fusion peptide using alkaline phosphatase. The fusion peptide can be placed at the C-terminus of Alk Phos with a RVRTKR (SEQ ID NO: 29) sequence separating the fusion peptide from Alk Phos.

To increase the promoter strength, a GAL4-NfkB p65 amplification system to amplify the promoter strength of a tissue specific promoter, is used. A plasmid containing a 6×GAL4 binding domain 5' to TATA box of the fusion peptide can be cotransfected with a plasmid containing the GAL4-P65 fusion protein driven by the CMV$_{enhancer}$/CBA$_{promoter}$. This can also be used for the proliferating endothelial promoter.

The CDKI (P14-ARF) domain represents 14 amino acids from a 132 amino acid protein and the first 35 amino acids are able to bind to mdm-2. This can easily be cloned into the expression cassette and analyzed. The same assays are used to test the expression of the peptide and the complete protein.

The potency of the CDKI can be increased by either expressing a more potent gene or a second cytotoxic gene that complements the activity of the CDKI. Another potential gene that has a very high degree of potency is the HSV-2 vhs (vector host shut off) protein. The vhs functions by degrading intracellular RNA so that the infected cell only synthesize viral transcripts. This is achieved with approximately 500 copies of protein per cell. The vhs protein are tested with the cell permeability peptides. Both the peptide targeted transfection complex and control of expression by the proliferating endothelial promoter are used for this protein.

A more linear approach is to express peptides that block cell cycle progression. A 10 mer peptide derived from P16 that can bind to cdk4 and cdk6 and inhibit cdk4-cyclin D1 kinase activity is to be used. Linkage of this peptide domain to an ANT domain results in blockage of cell entry into S phase for MCF-7 (breast cancer cell line) and HT-29 (colon carcinoma cell line). The 10 mer amino acid sequence, already shown to be amenable to membrane shuttling, can be put into the expression system as a second gene to augment the activity of the first gene. Both genes can be in the same plasmid under their own promoter. This is preferred to an IRES driven expression because the gene downstream from the IRES is usually expressed less than the upstream gene.

Example 21

HIV Tat and *Drosophila antenapedia* Homeodomain MPD for Delivery of Peptides

Peptides derived from HIV Tat and *Drosophila antenapedia homeodomain* were used to deliver a peptide sequence derived from the first exon of P14ARF that binds MDM-2, an oncoprotein upregulated in several types of cancer including brain cancer. Cellular uptake and cell killing were characterized in two human glioblastoma cell lines, a rat glioma cell line and rat cerebral arteries pressure-mounted in an arteriograph.

Materials and Methods

Peptides were synthesized and HPLC purified by the ICBR facility at the University of Florida. Sequence and complete deprotection was verified by MALDI mass spectroscopy. For fluorescent uptake studies, peptides were labeled with an N-terminal fluorescein. Biological activity was assessed with and without the fluorophore to ensure biological activity was due to the amino acid sequence.

Cell Lines

A172 cells, T98G cells and RG2 cells were purchased from ATCC. Cells were cultured under standard conditions. For cell uptake studies, each cell type was plated in 6 well plates at 5×105 cells per well 24 hours before the experiment. Increasing concentration of fluorescent peptides from 0.5 µM to 10 µM was prepared in complete medium. Cells were incubated with each concentration for 5, 10, 20 and 30 minutes at 37° C. followed by removal and washing of cells with 4° C. PBS 3x. Cells were solubilized in 0.2 ml 1% TX-100, PBS, pH 7.4. Fluorescence was measured using a fluorescent plate reader. Concentrations were determined by standard curve and normalized to µg of cellular protein.

Cell viability studies were performed by plating the cells under the same conditions as the uptake studies. Cells were incubated with fluorescent peptides for 1 hr at 37° C. The cells were removed from the plate using cell striper. They were labeled with propidium iodide and fluorescein-AM. Percent PI positive cells were determined by FACS.

For fluorescent microscopy studies cells were plated on 2 chamber cover slips at a density of $1 \times 10^4$ cells/chamber. Cells were incubated with 10 mM peptide for 30 minutes in completed media, washed with PBS 3x and imaged using a Nikon Axiophot inverted fluorescent microscope. Images were taken using a Spot CCD camera.

Rat Cerebral Artery Studies

Rats were anesthetized by intraperitoneal injection of pentobarbital sodium (160 mg/kg) and killed by decapitation. The brain was removed and placed in an ice-cold oxygenated physiological cerebrospinal fluid (PCSF, see below for composition). Cerebellar arteries were isolated and mounted in an arteriograph as described previously (Knot and Nelson 1998). The arteriograph was placed on an inverted microscope and the artery was visualized with a monochrome CCD camera coupled to a calibrated video caliper system to measure arterial diameter. The arteries were slowly pressurized to 70 mmHg under no flow conditions using a pressure servo-null system (Living Systems Inc., Burlington Vt.), and warmed to 37° C. while being continuously superfused (5 ml/min) with PCSF bubbled with 21% $O_2$, 5% $CO_2$, 74% $N_2$ (pH 7.35-7.40 in the bath). After an equilibration period of about 30 minutes at 70 mmHg, arteries showed stable constriction, myogenic tone. Myogenic tone is calculated by the following equation:

$$\text{Myogenic tone} = (Dp - Da)/Dp \times 100$$

where Da is the active diameter of the artery with myogenic tone and Dp is the passive diameter of the artery in the presence of calcium free PCSF at a particular intraluminal pressure.

In some experiments, the arterial segments were denuded of endothelium by passing an air bubble through the lumen, thus exposing the smooth muscle cells to luminally administered peptides. Constriction to pressure and 60 mM KCl and dilation of arteries with myogenic tone to 16 mM KCl were used as benchmarks of functional arteries. Peptide containing PCSF was perfused intraluminally at an inlet pressure of 70 mmHg with the outlet open, for 20 min and then perfused with normal PCSF. This procedure ensures a 20 min of exposure of the arteries to the peptide.

Effect of peptide on endothelial and smooth muscle function was evaluated by histamine (0.3 and 1 µM) and bradykinin (0.5 µM) (endothelium-dependent vasodilators) and 16 and 60 mM KCl (results in dilation and constriction of arteries by hyperpolarizing and depolarizing smooth muscle, respectively). These drug solutions were added to the superfusate and applied to the arteries extraluminally for 10 to 15 min before and after intraluminal perfusion with peptides. Effects of these agents were expressed as percent change in myogenic tone (decrease for dilators and increase for constrictors). Experiments were concluded by exposing the arteries to calcium free PCSF to obtain the passive diameter. Cell viability was determined by adding H3334 (Hoechst viability stain, final concentration 1 µM) and propidium iodide (final concentration 1 µM) to the arteriograph after the peptide incubation. Fluorescent micrographs were taken of the vessels after incubation with peptides and following addition of the vital stains using Till Photonics imaging system (Martinsried, Germany).

Statistics

Responses to dilators and constrictors before and after perfusion with peptides were compared by paired Students 't'-test using software program GraphPad Prism (San Diego, Calif.).

Glioma Cell Uptake Studies

A172, T98G and RG2 cells were plated in 6 well plates and incubated with 1, 2.5, 5 and 10 uM fluorescein labeled peptides for 5, 15, 30 and 60 minutes. Cells were washed 3× with PBS, removed from the plates with trypsin, centrifuged for 2 minutes at 2K rpm in a desk top centrifuge, supernatants discarded and the cell pellets were solubilized in 1% TX-100, PBS, pH 7.4. Fluorescence was measured in a Perkin Elmer fluorimeter using ~ex=480 nm and ~em=520 nm with a 510 nm cut off filter. Amount of cell-associated protein was determined from the standard curve.

Results

Synthetic peptides derived from HIV Tat (Tat) and the Drosophila antennaepedia homeodomain (ANT) were tested for cell uptake by A172 cells (human glioblastomas). The peptides were labeled at the N-terminus with fluorescein. Cells were incubated with 30 uM peptide at 37° C. in serum containing media. Fluorescent micrographs were taken after 1 hr incubation at 37° C. Tat peptide yielded intracellular punctate. The ANT peptide yielded similar intracellular periplasmic punctate staining. The fluorescent intensity was greater for the ANT peptide than the Tat peptide for both cell types, indicating a higher degree of cell uptake compared to the Tat peptide. The size of the peptide was increased by added an Mdm-2 binding domain derived from P14ARF. This domain was added to the C-terminus of the Tat and ANT peptides. The P14ARF domain was also placed at the N-terminus followed by the Tat peptide. The sequences for all the peptides are shown in Table 6. All the peptides were labeled at the N-terminus with fluorescein and cell incubations similar to the Tat and ANT peptides were tested for cellular uptake. The results show uptake of the ANTP 14ARF for A172 cells. Upon gross observation, the staining pattern and intensity are similar to that observed for ANT alone. Hence, addition of the P 14ARF domain did not inhibit cell uptake. However, the Tat-P14ARF and P14ARF-Tat show nuclear staining compared to the Tat peptide. Both the bright field and fluorescent micrographs show altered cell morphology. The P14ARF-Tat peptide also showed reduced cell density in that many of the cells began lifting off the plate during the 1-hour incubation.

To show that these observations were not restricted to A172 cells, peptide uptake was tested in RG2 cells, a rat glioma cell line. Incubation of ANT-P14ARF with RG2 cells yielded similar intracellular punctate staining patterns to that observed for A172 cells. Similar staining patterns were observed for the Tat-P14ARF and P14ARF-Tat. Both peptides yielded nuclear staining compared to the intracellular punctate staining observed with ANT-P14ARF. Also similar altered cell morphologies for both Tat-P14ARF and P14ARF-Tat were observed for in both bright field and fluorescence. Finally, the P14ARF-Tat showed reduced cell density compared to TatP14ARF. Similar observations were obtained for all the peptides in another human glioblastoma cell line, T98G.

The cytotoxicity of the chimeric peptides was characterized using a cell viability assay. Peptides were added to cells at a fixed concentration. After a 30-minute incubation, cells were removed from the plate, stained with propidium iodide and the % positive cells were determined by FACS (fluorescent activated cell scanning). The test conditions were Tat, ANT, Tat-P14ARF, ANT-P14ARF and P14ARF. T98G cells were tested along with RG2 cells and A172 cells. The Tat-P14ARF and ANT-P14ARF killed 60 to 70% of the three cell types. No impact on cell viability was observed for Tat or ANT peptides. A slight reduction in cell viability was observed for P14ARF in RG2 cells (22%).

The Tat-P14ARF displayed the highest degree of cell killing in all three cell types and also showed nuclear localization from the fluorescent cell labeling studies. This peptide was further characterized with regard to dose response. In addition, the human and rat P14ARF sequences were compared for activity in the rat RG2 glioma cell line. A linear dose response was observed from 1 µM to 10 µM peptide for all three peptides tested. The Tat-humanP14ARF and Tat-rat P14ARF both yielded superimposable dose response curves ($IC_{50}$~10 µM). The human p14ARF Tat was more effective yielding a 3 µM $IC_{50}$. Kinetic uptake studies were performed with the same cell line for all three peptides plus a PTD5 peptide reported to have similar cell penetration activity for several cell lines. The results show that Tat alone had a more rapid uptake than TatP14ARF. However, P14ARF-Tat had a similar uptake rate possible explaining why this chimeric peptide had a lower $IC_{50}$. The PTD5 peptide had a much slower uptake rate than Tat. This was further verified by fluorescence microscopy, which showed no cellular fluorescence at the same concentration as the Tat and ANT peptides.

These studies were conducted in tissue culture using both human and rat brain cancer cells. It is of interest to determine the uptake properties and biological activity of these peptides on non-transformed cells. Uptake properties of these peptides were tested in endothelial cells using intact blood vessels. Cerebellar arteries were isolated from rat brains, pressure-mounted in an arteriograph and intraluminally perfused with peptides. Cell uptake was first established by testing the cell penetration domains by themselves. The results for the Tat peptide show that he Tat peptide displayed a dashed staining pattern selectively labeling the endothelial nuclei. What is not observed is the fluorescent labeling of the smooth muscle cells wrapping around the blood vessel perpendicularly. There is a breach in the endothelial cell layer showing that smooth muscle cells are being labeled at this breach. The fluorescent ANT peptide displayed a continuous string-staining pattern that represented cytoplasmic staining of the endothelial cells. Both peptides only labeled the endothelial cells and did not label the smooth muscle cells surrounding the endothelial cells. Ektraluminal addition of both ANT and Tat peptides were able to label the smooth muscle cells.

Intraluminal addition of Tat-P14ARF peptide yielded the same labeling pattern as the Tat alone. However, within 15 minutes after addition, the morphology of the endothelial cells was altered displaying a more disorganized staining pattern. The biological activity of these peptides was assayed in two ways. The first: was to evaluate the effect of the peptides on the biological function of smooth muscle and endothelium. Responses to different constrictors and dilators in arteries with myogenic tone were obtained before and after the intraluminal exposure of arteries to peptides. The results show the constriction and dilation response to 60 and 16 mM KCl, respectively, which was not affected by Tat-P14ARF peptide. However, endothelium-dependent dilation to histamine (0.3 and 1 µM) and bradykinin (0.5 µM) were significantly reduced by the Tat-P14ARF peptide compared to that before treatment. Both the endothelial cells and smooth muscle are responsive to all stimuli when treated with Tat or P14ARF peptides.

Cell viability was tested by staining the blood vessels with H3334 and propidium iodide after treatment with peptide. The results show blue staining of perpendicular nuclei staining indicative of live smooth muscle cells. There are some horizontal blue nuclei indicative of endothelial cells. The propidium iodide staining shows predominantly horizontal endothelial nuclei being stained indicating cell death. Both the cell viability staining and the functional studies show that intraluminal administration of the Tat-P14ARF peptide was able to selectively affect the endothelial cells but not the smooth muscle cells.

TABLE 6

| Peptide Name | Peptide Sequence |
|---|---|
| HIV Tat (Tat) | AGGGYGRKKRRQRRR (SEQ ID NO: 30) |
| Antennaepedia Homeodomain (ANT) | RQIKIWFQNRRMKWKK (SEQ ID NO: 9) |
| [a]Human P14ARF | MVRRFLVTLRIRRA (SEQ ID NO: 10) |
| Rat P19ARF | MGRRFVVTVRIRRT[b] (SEQ ID NO: 31) |
| Tat-P14ARF | AGGGYGRKKRRQRRR MVRRFLVTLRIRRA (SEQ ID NO: 32) |
| P14ARF-Tat | MVRRFLVTLRIRRA-AGGGYGRKKRRQRRR (SEQ ID NO: 33) |
| ANT-P14RF | RQIKIWFQNRRMKWKK-MVRRFLVTLRIRRA (SEQ ID NO: 34) |

[a]P14ARF is amino acids 1 to 14 of human P14 ARF, also referred to as cyclin-dependent kinase inhibitor 2A.
[b]Rat P19ARF (accession no.:AF474975) is the same protein as P14ARF in humans While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

All references cited herein, are incorporated herein by reference.

What is claimed is:

1. An expression vector comprising a nucleic acid encoding a fusion protein comprising a cell membrane permeability domain having an amino acid sequence, SEQ ID NO:1, and a cell toxicity domain, p19.

2. The vector of claim 1, further comprising a promoter that selectively drives expression of the fusion protein in endothelial cells.

3. The vector of claim 2, further comprising a promoter that selectively drives expression of the fusion protein in proliferating cells.

4. The vector of claim 3, wherein the promoter is 4×ETe/cdc6.

* * * * *